(12) United States Patent
Bouillon et al.

(10) Patent No.: US 7,704,986 B2
(45) Date of Patent: Apr. 27, 2010

(54) VITAMIN $D_3$ ANALOGUES FOR THE PREVENTION AND TREATMENT OF BONE DISORDERS

(75) Inventors: Roger Bouillon, Winksele (BE); Annemieke Verstuyf, Oud-Heverlee (BE); Pierre De Clercq, Gent (BE); Maurits Vandewalle, Gent (BE)

(73) Assignees: K.U. Leuven Research and Development, Leuven (BE); Universiteit Gent, Gent (BE)

( * ) Notice: Subject to any disclaimer, the term of this patent is extended or adjusted under 35 U.S.C. 154(b) by 204 days.

(21) Appl. No.: 11/577,254

(22) PCT Filed: Oct. 17, 2005

(86) PCT No.: PCT/BE2005/000146

§ 371 (c)(1),
(2), (4) Date: Apr. 13, 2007

(87) PCT Pub. No.: WO2006/039763

PCT Pub. Date: Apr. 20, 2006

(65) Prior Publication Data

US 2008/0032955 A1     Feb. 7, 2008

(30) Foreign Application Priority Data

Mar. 15, 2004    (GB) ................... 0422929.0

(51) Int. Cl.
*A01N 43/00* (2006.01)
*A61K 31/33* (2006.01)

(52) U.S. Cl. ........................................ 514/183
(58) Field of Classification Search .................. 514/183
See application file for complete search history.

(56) References Cited

U.S. PATENT DOCUMENTS 6,017,907 A    1/2000   Bouillon et al.
6,548,715 B1    4/2003   Bouillon et al.

OTHER PUBLICATIONS

Wu et al., "Vitamin $D_3$: Synthesis of seco-C-9, 11-bisnor-17-Methyl-1 α, 25-dihydroxyvitamin $D_3$ Analogues," *Bioorg Med Chem Lett.* 12(12):1633-6 (2002).
International Search Report (PCT/BE2005/000146).
Written Opinion (PCT/BE2005/000146).
International Preliminary Report on Patentability (PCT/BE2005/000146).

*Primary Examiner*—Brandon J Fetterolf
*Assistant Examiner*—Jean Cornet
(74) *Attorney, Agent, or Firm*—Clark & Elbing LLP

(57) ABSTRACT

Novel vitamin D analogues are useful for making pharmaceutical compositions for the prevention or treatment of bone disorders such as osteoporosis.

7 Claims, 13 Drawing Sheets

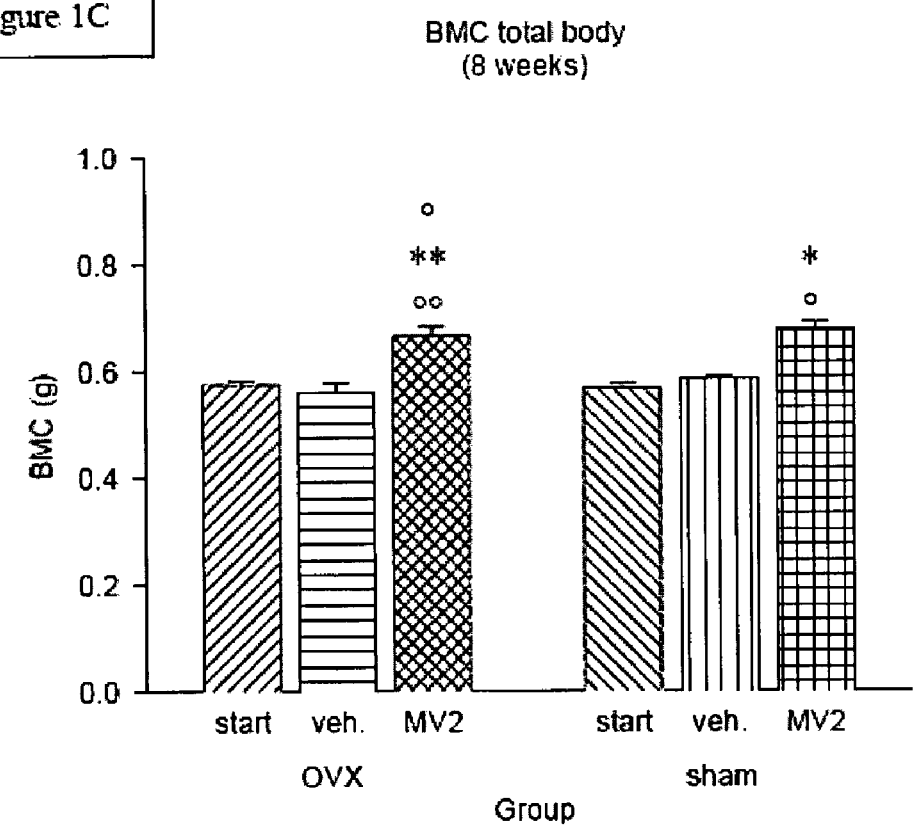

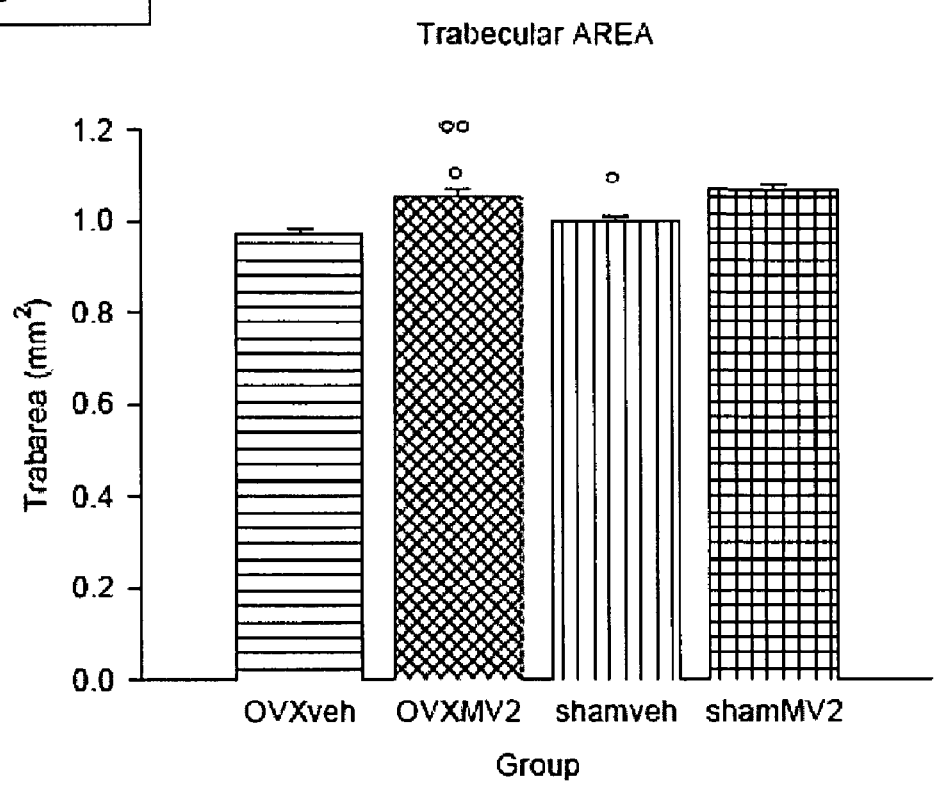

Femur Calcium (8 weeks)

Serum Calcium (8 weeks)

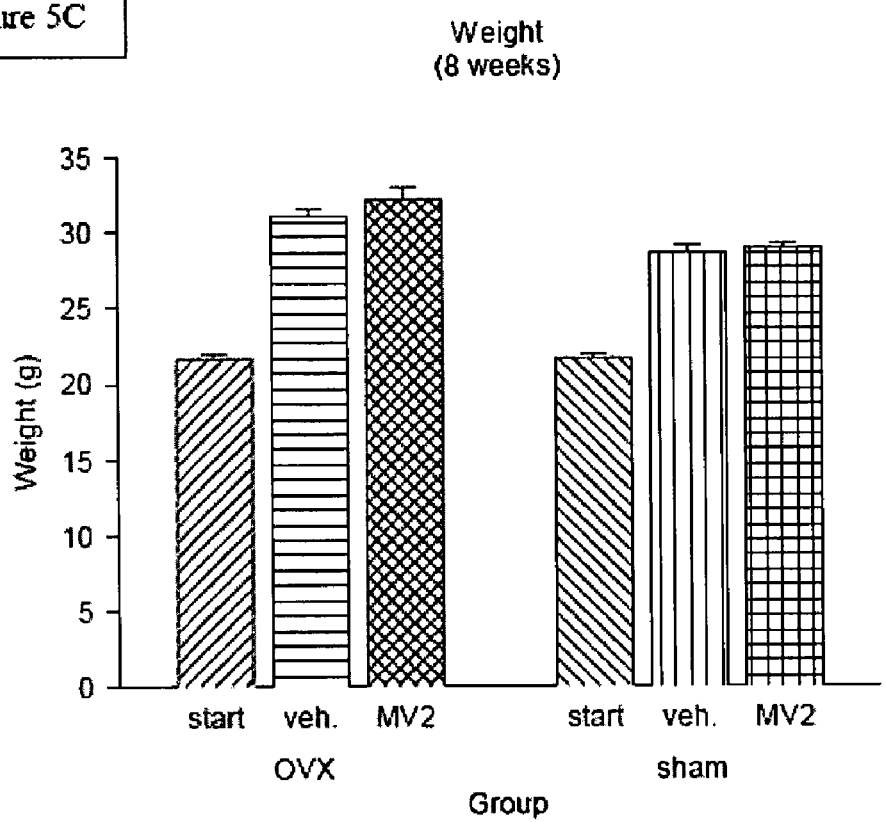

VITAMIN $D_3$ ANALOGUES FOR THE PREVENTION AND TREATMENT OF BONE DISORDERS

CROSS-REFERENCE TO RELATED APPLICATIONS

This application is the U.S. National Stage of International Application Ser. No. PCT/BE2005/000146, filed Oct. 17, 2005, which, in turn, claims benefit of British Patent Application Ser. No. 0422929.0, filed Oct. 15, 2004.

FIELD OF THE INVENTION

The present invention relates to vitamin $D_3$ analogues. The present invention further relates to pharmaceutical compositions comprising therapeutically effective amounts of such vitamin $D_3$ analogues, as well as methods of using such vitamin $D_3$ analogues, e.g. in the prevention and treatment of bone disorders such as, but not limited to, bone loss, osteomalacia, renal osteodystrophy, Paget's disease and osteoporosis, without inducing hypercalcemia in humans and other mammals.

BACKGROUND OF THE INVENTION

Calcitriol ($1\alpha,25(OH)_2D_3$) is the hormonally active metabolite of vitamin $D_3$. Calcitriol functions not only in the calcium homeostatic mechanisms and in support of bone mineralization but also elsewhere, inter alia, parathyroid glands, the keratinocytes, and cells of the immune system.

Primarily, calcitriol functions to elevate plasma calcium and plasma phosphorous to support bone mineralization and also to prevent neuromuscular convulsions. However, calcitriol has the effect of inducing elevated plasma calcium concentrations (hypercalcemia) when given in amounts believed to be sufficient to overcome the effects of osteoporosis.

U.S. Pat. No. 6,017,907 describes the synthesis and biological activities of a group of vitamin D analogues, including C/D cis-fused analogues. The biological activities described in this document refer to inhibition of cell proliferation, induction of cell differentiation, treatment and prevention of immune disorders, inflammatory diseases, skin disorders, hyperproliferative disorders and cancer, and improving the function of cells in which calcium is an essential regulating agent. U.S. Pat. No. 6,017,907 teaches, based on FIG. 6 showing an evaluation in rachitic chicks after treatment for ten consecutive days with three individual compounds referred as 4, 5 and 58, by measuring serum and bone calcium and serum osteocalcin, that these vitamin D analogues have strikingly lower effect on calcium and bone homoeostasis, i.e. do not have the same toxic effect as previously known vitamin D compounds. U.S. Pat. No. 6,017,907 however does not teach or suggest using these vitamin D analogues for the therapy or prevention of bone disorders such as osteoporosis, renal osteodystrophy, Paget's disease or osteomalacia.

Wu et al. in *Bioorganic & Medicinal Chemistry Letters* (2002) 12: 1633-1636 have disclosed the synthesis of a few seco-C-9,11-bisnor-17-methyl-$1\alpha$,25-dihydroxyvitamin $D_3$ analogues. By determining their biological activities in vitro on different cell lines, they have showed that antiproliferative activities are high, the S-epimer being the more potent within a pair of 20-epimers, and that several analogues display high ratios of differentiation between antiproliferative and calcemic effects. This document however does not teach or suggest using these vitamin $D_3$ analogues for the therapy or prevention of bone disorders such as osteoporosis, renal osteodystrophy, Paget's disease or osteomalacia.

There is a need in the art for vitamin $D_3$ analogues being potent bone protecting agents by selectively targeting bone formation rather than bone resorption or intestinal calcium absorption, thus leading to less calcemic effects (such as hypercalcemia or hypercalciuria) than $1,25(OH)_2D_3$. There is also a need in the art for vitamin $D_3$ analogues which are both efficient and safe in the treatment of bone disorders such as, but not limited to, osteoporosis, renal osteodystrophy, Paget's disease or osteomalacia.

There is a long felt need in the art for vitamin $D_3$ compounds which have the ability to bind to the Vitamin D Receptor (VDR) and induce bone matrix formation and mineralization without the potential side effects of hypercalcemia.

SUMMARY OF THE INVENTION

In one embodiment, the present invention relates to the Vitamin $D_3$ analogue (1R,3R)-5-{(E)-3-((1S,3R)-3-((1S,4R)-4-hydroxy-1,5-dimethylhexyl)-2,2,3-trimethylcyclopentyl)-2-propenylidene)cyclohexane-1,3-diol and its diastereoisomer having the following structural formulae:

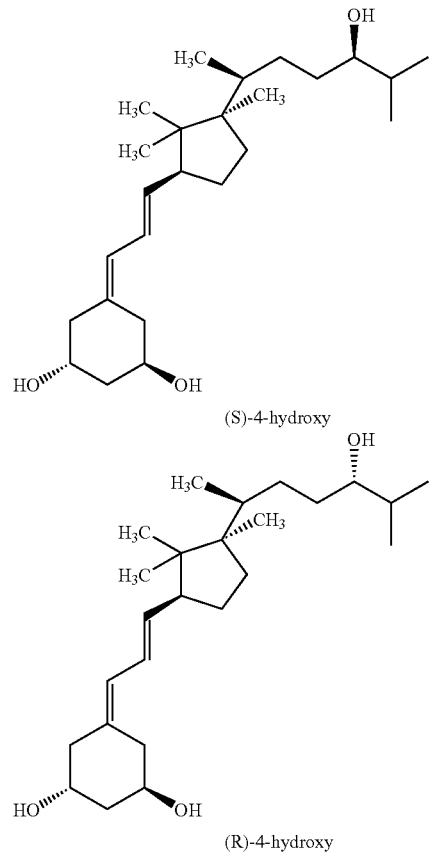

In another embodiment, the present invention also relates to pharmaceutical compositions comprising:

A) a therapeutically effective amount of (1R,3R)-5-{(E)-3-[(S)-3-((S)-4-hydroxy-1-(S)-methyl-5-methylhexyl)-2,2,3-trimethyl-cyclopentyl]-allylidene}-cyclohexane-1,3-diol and/or one or more diastereomers thereof, and B) one or more pharmaceutically acceptable excipients, diluents or carriers, said compositions being especially useful for controlling, in particular preventing or treating, bone disorders such as, but not limited to, osteoporosis, renal osteodystrophy, Paget's disease or osteomalacia.

In another embodiment, the present invention further relates to a method for controlling, in particular preventing or treating, bone disorders such as, but not limited to, osteoporosis, renal osteodystrophy, Paget's disease or osteomalacia, said method comprising administering to a human or another mammal a therapeutically effective amount of (1R,3R)-5-{(E)-3-[(S)-3-((S)-4-hydroxy-1-(S)-methyl-5-methyl-hexyl)-2,2,3-trimethyl-cyclopentyl]-allylidene}-cyclohexane-1,3-diol and/or the (R)-4-hydroxy diastereomer thereof.

In another embodiment, the present invention relates to another vitamin $D_3$ analogue, (1R,3S)-5-((Z,2E)-3-((1S,3R)-3-((1S,4S)-4-hydroxy-1,5-dimethylhexyl)-2,2,3-trimethyl-cyclopentyl)-2-propenylidene)-4-methylene-cyclohexane-1,3-diol, having the structural formula:

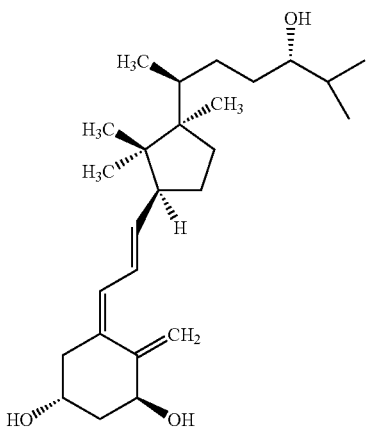

In another embodiment, the present invention also relates to pharmaceutical compositions comprising:
  (A) a therapeutically effective amount of (1R,3S)-5-((Z,2E)-3-((1S,3R)-3-((1S,4S)-4-hydroxy-1,5-dimethyl-hexyl)-2,2,3-trimethylcyclopentyl)-2-propenylidene)-4-methylene-cyclohexane-1,3-diol, and
  (B) one or more pharmaceutically acceptable excipients, diluents or carriers, said compositions being especially useful for controlling, in particular preventing or treating, bone disorders such as, but not limited to, osteoporosis, renal osteodystrophy, Paget's disease or osteomalacia.

In another embodiment, the present invention further relates to a method for controlling, in particular preventing or treating, bone disorders such as, but not limited to, osteoporosis, renal osteodystrophy, Paget's disease or osteomalacia, said method comprising administering to a human or another mammal a therapeutically effective amount of (1R,3S)-5-((Z,2E)-3-((1S,3R)-3-((1S,4S)-4-hydroxy-1,5-dimethyl hexyl)-2,2,3-trimethylcyclopentyl)-2-propenylidene)-4-methylene-cyclohexane-1,3-diol.

In another embodiment, the present invention relates to another vitamin $D_3$ analogue, (1R,3S)-5-((Z,2E)-3-((1S,3R)-3-((1S,4R)-4-hydroxy-1,5-dimethylhexyl)-2,2,3-trimethyl-cyclopentyl)-2-propenylidene)-4-methylene-cyclohexane-1,3-diol, having the structural formula:

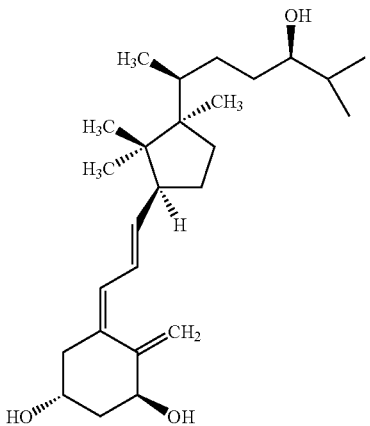

In another embodiment, the present invention also relates to pharmaceutical compositions comprising:
  (A) a therapeutically effective amount of (1R,3S)-5-((Z,2E)-3-((1S,3R)-3-((1S,4R)-4-hydroxy-1,5-dimethyl-hexyl)-2,2,3-trimethylcyclopentyl)-2-propenylidene)-4-methylene-cyclohexane-1,3-diol, and
  (B) one or more pharmaceutically acceptable excipients, diluents or carriers, said compositions being especially useful for controlling, in particular preventing or treating, bone disorders such as, but not limited to, osteoporosis, renal osteodystrophy, Paget's disease or osteomalacia.

In another embodiment, the present invention further relates to a method for controlling, in particular preventing or treating, bone disorders such as, but not limited to, osteoporosis, renal osteodystrophy, Paget's disease or osteomalacia, said method comprising administering to a human or another mammal a therapeutically effective amount of (1R,3S)-5-((Z,2E)-3-((1S,3R)-3-((1S,4R)-4-hydroxy-1,5-dimethylhexyl)-2,2,3-trimethylcyclopentyl)-2-propenylidene)-4-methylene-cyclohexane-1,3-diol.

In yet another embodiment, the present invention further relates to a method for controlling, in particular preventing or treating, bone disorders such as, but not limited to, osteoporosis, renal osteodystrophy, Paget's disease or osteomalacia, said method comprising administering to a human or another mammal a therapeutically effective amount of a vitamin $D_3$ analogue selected from the group consisting of:
  (1R,3S)-5-((Z,2E)-3-((1S,3R)-3-((1S)-6,6,6-trifluoro-5-hydroxy-1-methyl-5-trifluoromethyl-3-hexynyl)-2,2,3-trimethylcyclopentyl)-2-propenylidene)-4-methylenecyclohexane-1,3-diol,
  (1R,3S)-5-((Z,2E)-3-((1S,3R)-3-((1R)-6,6,6-trifluoro-5-hydroxy-1-methyl-5-trifluoromethyl-3-hexynyl)-2,2,3-trimethylcyclopentyl)-2-propenylidene)-4-methylenecyclohexane-1,3-diol,
  (1R,3S)-5-((Z,2E)-3-((1S,3R)-3-((1R)-5-hydroxy-1,5-dimethyl-3-hexynyl)-2,2,3-trimethylcyclopentyl)-2-propenylidene)-4-methylenecyclohexane-1,3-diol,
  (1R,3S)-5-((Z,2E)-3-((1S,3R)-3-((1S)-6,6,6-trifluoro-5-hydroxy-1-methyl-5-(trifluoromethyl)hexyl)-2,2,3-trimethylcyclopentyl)-2-propenylidene)-4-methylenecyclohexane-1,3-diol,
  (1R,3S)-5-((Z,2E)-3-((1S,3R)-3-((1R)-6,6,6-trifluoro-5-hydroxy-1-methyl-5-(trifluoromethyl)hexyl)-2,2,3-trimethylcyclopentyl)-2-propenylidene)-4-methylenecyclohexane-1,3-diol, (1R,3R)-5-((E)-3-((1S,3R)-3-((1R)-6,6,6-trifluoro-5-hydroxy-1-methyl-5-trifluoromethyl-3-hexynyl )-2,2,3-trimethylcyclopentyl)-2-propenylidene)cyclohexane-1,3-diol, and (1R,3R)-5-((E)-3-((1S,3R)-3-((1S)-5-ethyl-5-hydroxy-1-methylheptyl)-2,2,3-trimethylcyclopentyl)-2-propenylidene)cyclohexane-1,3-diol.

These and other objects, features, and advantages will become apparent to those of ordinary skill in the art from a reading of the following detailed description and the appended claims.

BRIEF DESCRIPTION OF THE DRAWINGS

In all drawings, the values shown represent mean±SEM (n=9-13 in FIGS. 1 to 5, n=8-10 in FIGS. 6 to 11). One-way analysis of variance (ANOVA) was carried out to detect overall differences and if P was less than 0.05, was followed by Fisher's least-significant-difference multiple-comparison test to calculate intergroup differences.

Bone mineral density (BMD) and bone mineral content (BMC) were measured by dual-energy X-ray absorptiometry (DEXA) and/or Peripheral Quantitative Computed Tomography (pQCT).

significantly different from OVX start (**)
significantly different from SHAM start (*)
significantly different from OVX mice treated with vehicle (°°)
significantly different from SHAM mice treated with vehicle (°)
significantly different from OVX mice treated with MV2 (°°°)

Figure 2A:
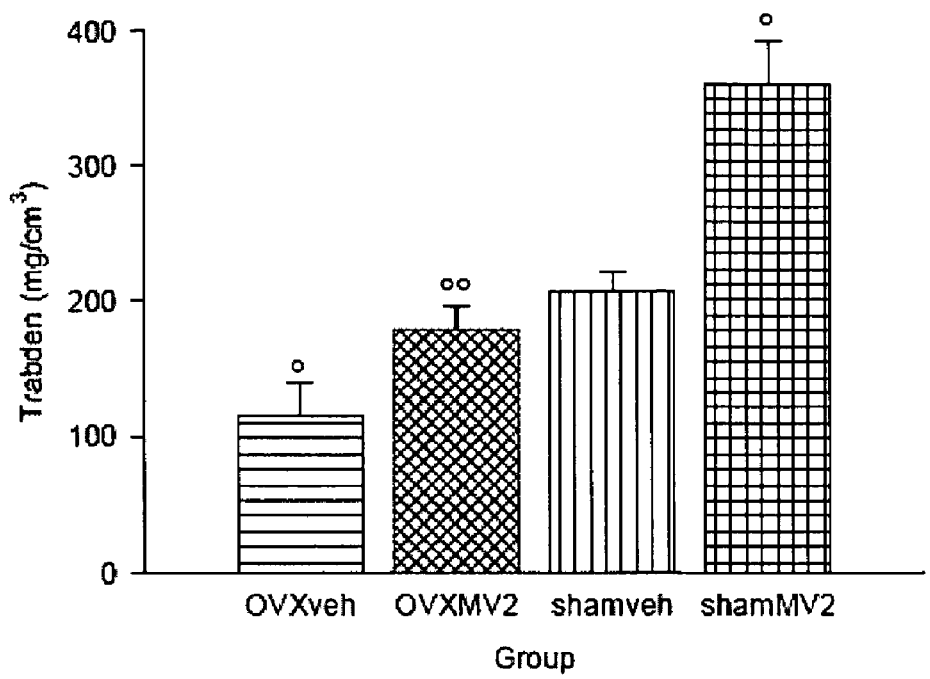
Figure 2B:
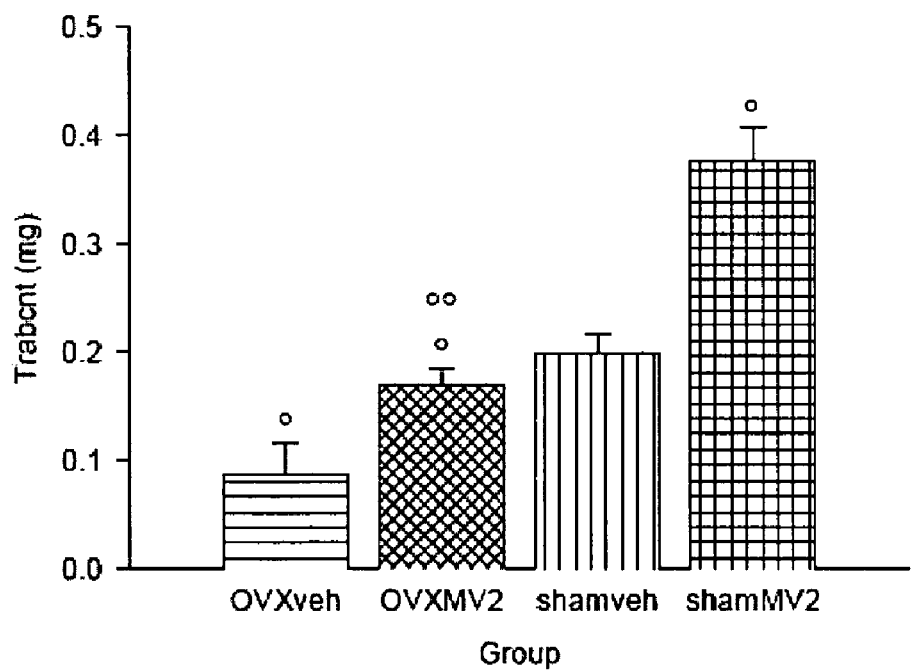

FIG. 2 shows data of the following experiment: 12-week old C3H mice were SHAM or OVX operated and treated with MV2 (0.5 µg/kg/d i.p.) or vehicle (veh., arachis oil) during 8 weeks. Trabecular bone mineral density (BMD, FIG. 2A), trabecular bone mineral content (BMC, FIG. 2B) and trabecular area (FIG. 2C) of the femur were assessed by pQCT and are accompanied by the following notations:

significantly different from OVX mice treated with vehicle (°°)
significantly different from SHAM mice treated with vehicle (°)

FIG. 3 shows data of the following experiment: 12-week old C3H mice were SHAM or OVX operated and treated with MV2 (0.5 µg/kg/d i.p.) or vehicle (veh., arachis oil) during 8 weeks. Cortical bone mineral density (BMD, FIG. 3A) and bone mineral content (BMC, FIG. 3B) of the femur were assessed by pQCT. Periosteal circumference (FIG. 3C), endosteal circumference (FIG. 3D), area (FIG. 3E) and thickness (FIG. 3F) of the cortex were determined and their data are accompanied by the following notations:

significantly different from OVX mice treated with vehicle (°°)
significantly different from SHAM mice treated with vehicle (°)

Figure 4A:
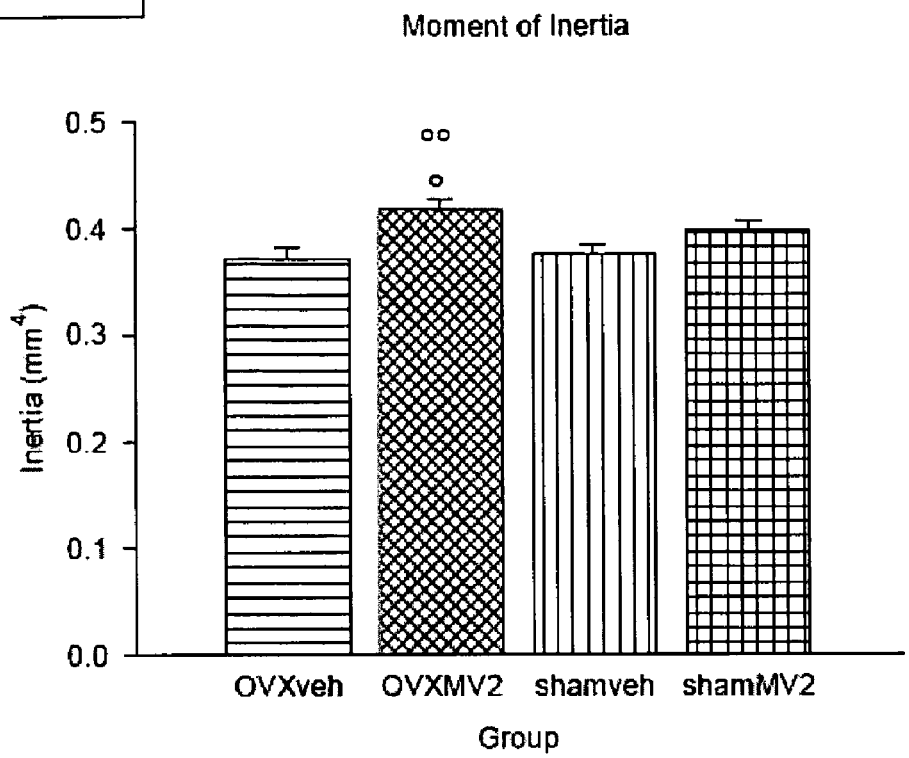
Figure 4B:
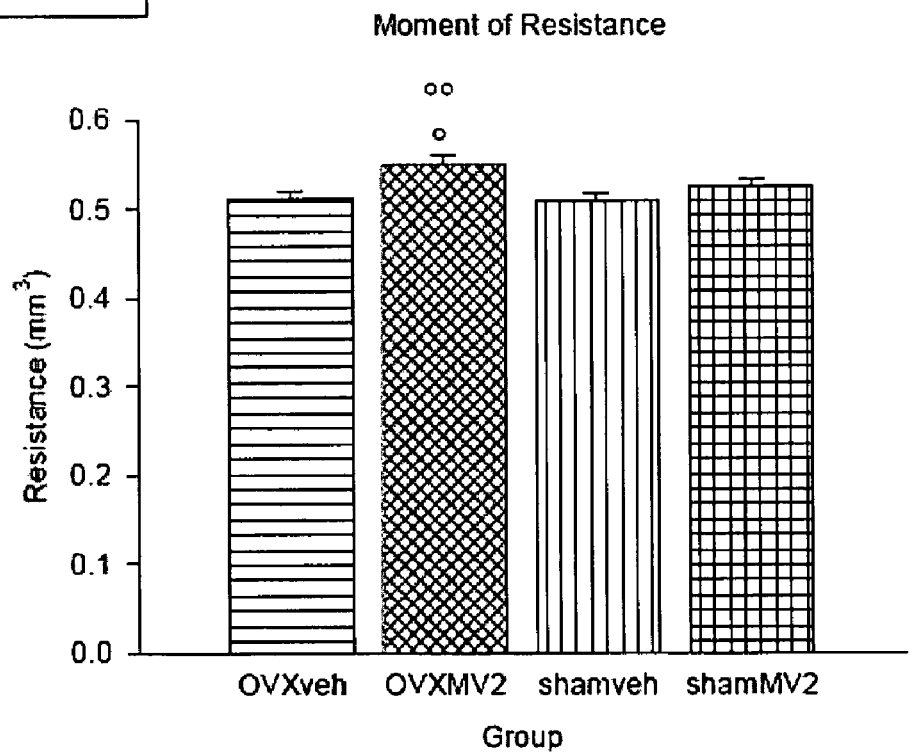

FIG. 4 shows data of the following experiment: 12-week old C3H mice were SHAM or OVX operated and treated with MV2 (0.5 µg/kg/d i.p.) or vehicle (veh., arachis oil) during 8 weeks. Moment of inertia (FIG. 4A) and moment of resistance (FIG. 4B) were calculated based on the pQCT measurements and data are accompanied by the following notations:

significantly different from OVX mice treated with vehicle (°°)
significantly different from SHAM mice treated with vehicle (°)

Figure 5A:
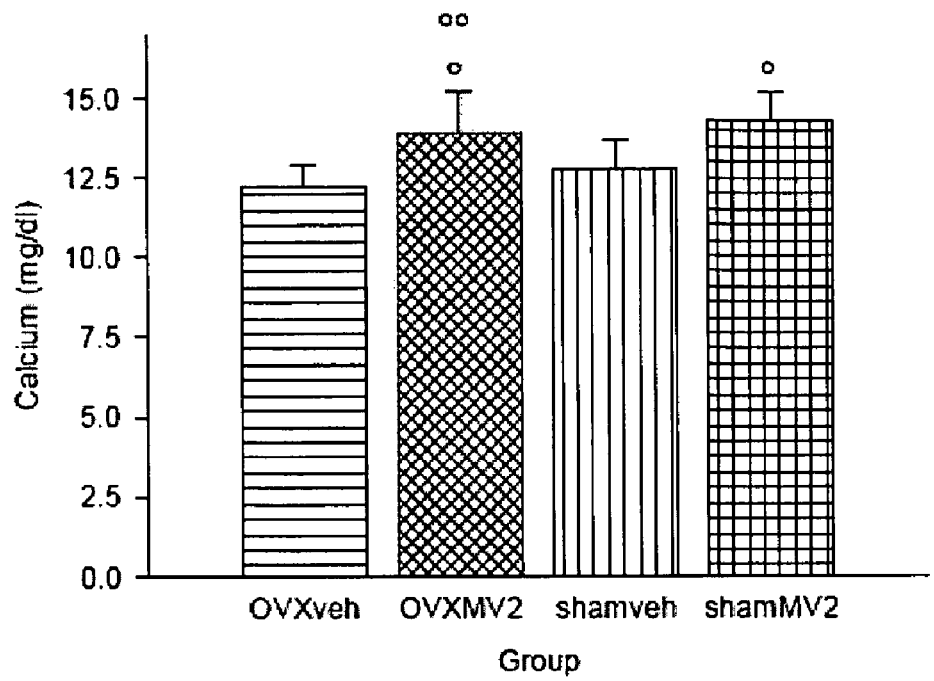
Figure 5B:
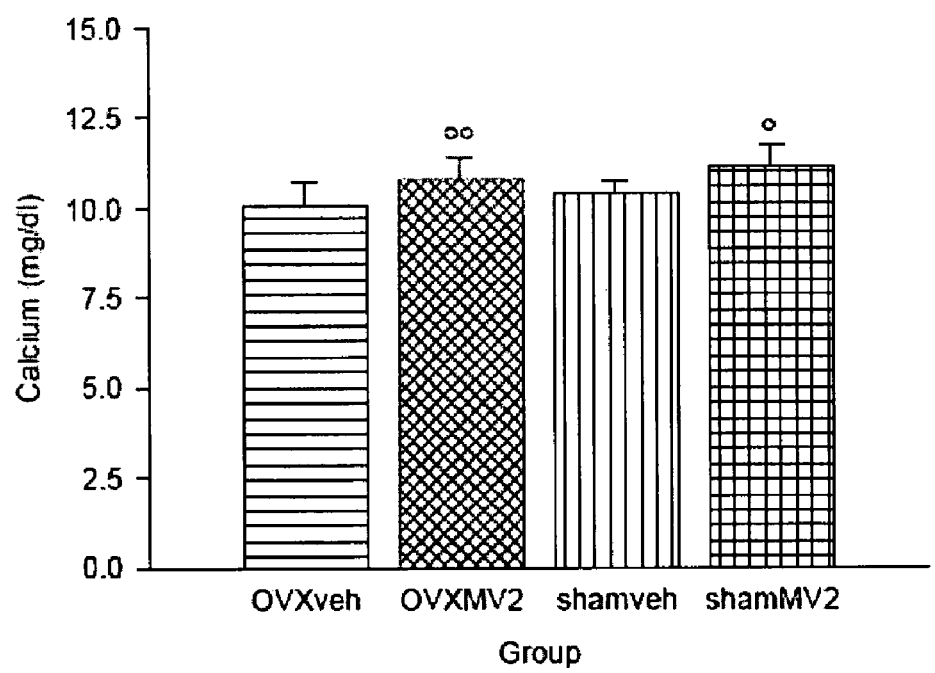

FIG. 5 shows data of the following experiment: 12-week old C3H mice were SHAM or OVX operated and treated with MV2 (0.5 µg/kg/d i.p.) or vehicle (veh., arachis oil) during 8 weeks. Calcium levels were determined at the end of the experiment in femur (FIG. 5A) and serum (FIG. 5B). Weights of the animals were measured at the beginning and the end of the experiment (FIG. 5C) and data are accompanied by the following notations:

significantly different from OVX mice treated with vehicle (°°)
significantly different from SHAM mice treated with vehicle (°)

Figure 6:
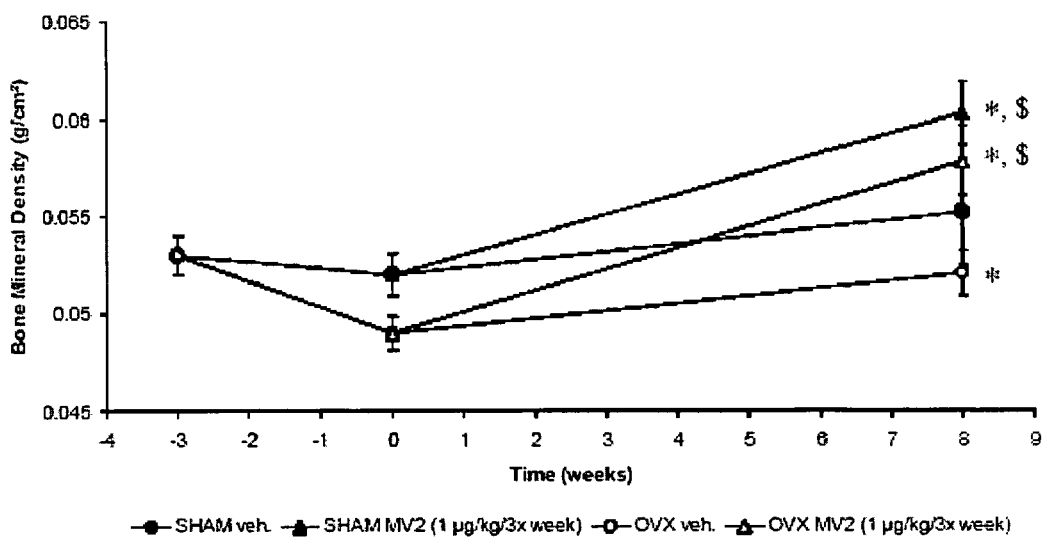

FIG. 6 shows data of the following experiment: 12-week old C3H mice were SHAM or OVX operated (time −3). Three weeks after the ovariectomy treatment was started (time 0) with MV2 (1 µg/kg three times per week p.o.) or vehicle (veh., arachis oil) during 8 weeks. BMD data are accompanied by the following notations:

* significantly different from SHAM mice treated with vehicle, and
$ significantly different from OVX mice treated with vehicle.

Figure 7:
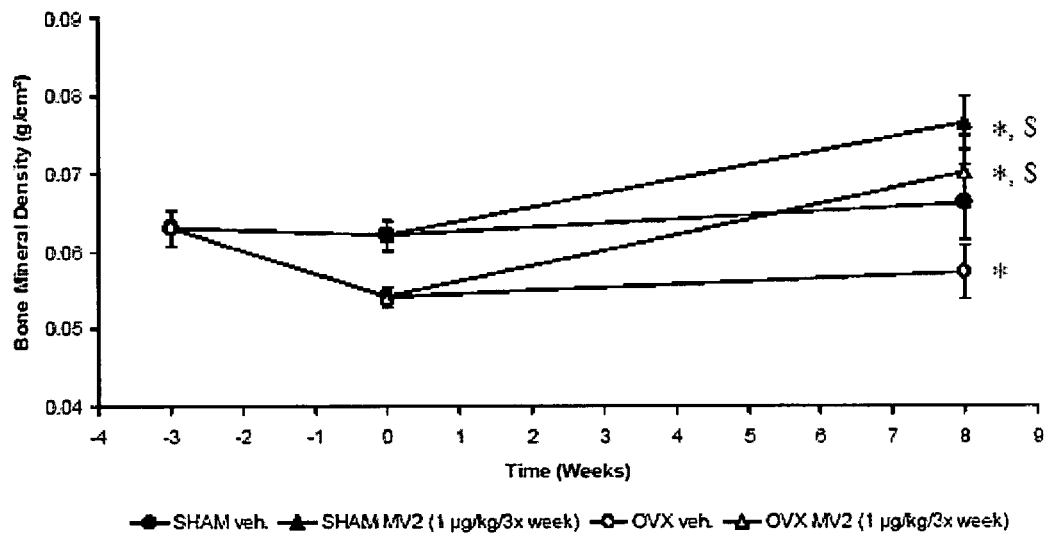

FIG. 7 shows data of the following experiment: 12-week old C3H mice were SHAM or OVX operated (time −3). Three weeks after the ovariectomy treatment was started (time 0) with MV2 (1 µg/kg/3 times per week p.o.) or vehicle (veh., arachis oil) during 8 weeks. BMD data of spine are accompanied by the following notations:

* significantly different from SHAM mice treated with vehicle, and
$ Significantly different from OVX mice treated with vehicle.

Figure 8:
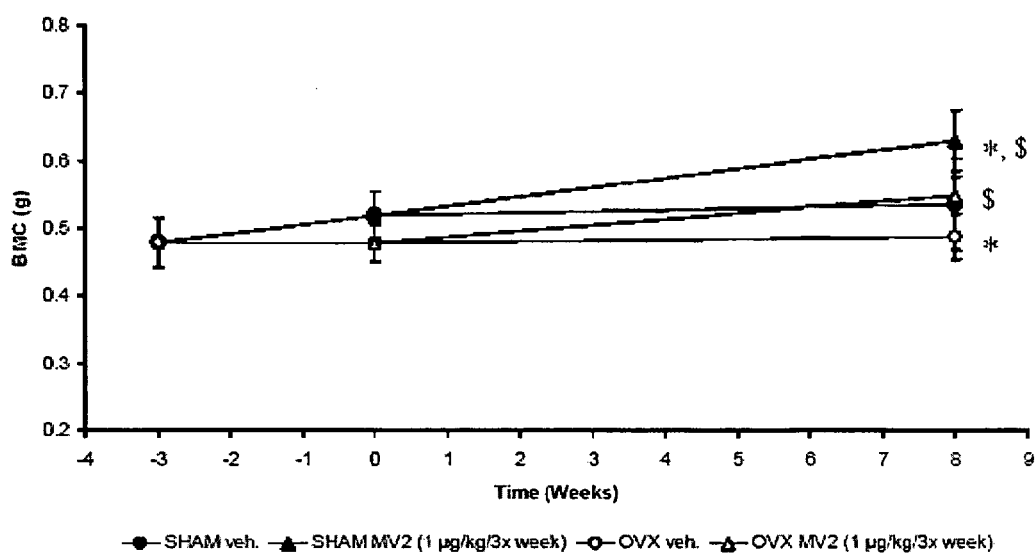
Figure 9:
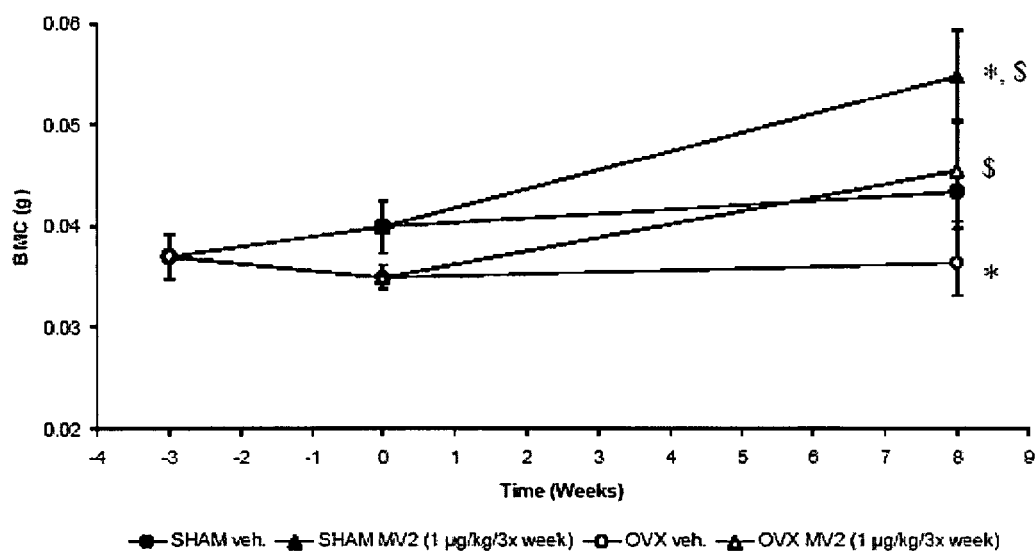

FIG. 8 shows data of the following experiment: 12-week old C3H mice were SHAM or OVX operated (time −3). Three weeks after the ovariectomy treatment was started (time 0) with MV2 (1 µg/kg three times per week p.o.) or vehicle (veh, arachis oil) during 8 weeks. BMC data of total body are accompanied by the following notations:

* significantly different from SHAM mice treated with vehicle, and
$ significantly different from OVX mice treated with vehicle FIG. 9 shows data of the following experiment: 12-week old C3H mice were SHAM or OVX operated (time −3). Three weeks after the ovariectomy treatment was started (time 0) with MV2 (1 µg/kg three times per week p.o.) or vehicle (veh., arachis oil) during 8 weeks. BMC data of spine are accompanied by the following notations:

* significantly different from SHAM mice treated with vehicle, and
$ significantly different from OVX mice treated with vehicle.

Figure 10:
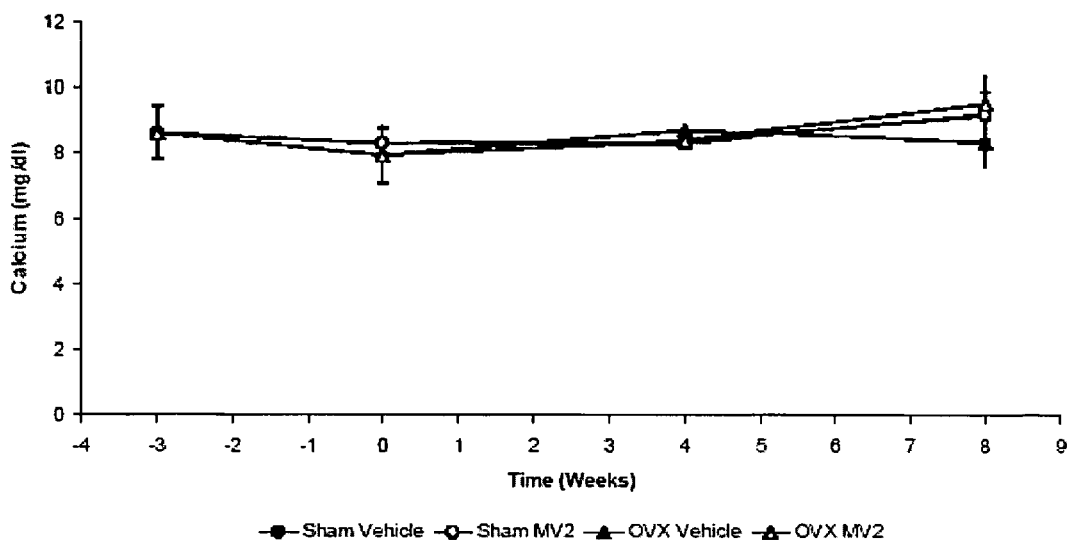
Figure 11:
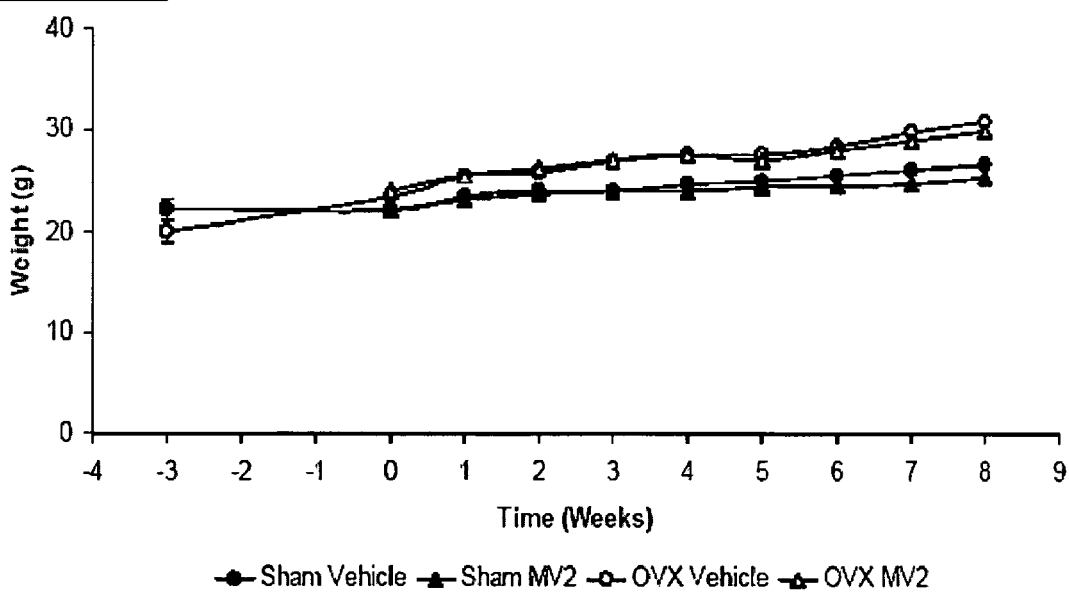

FIG. 10 shows data of the following experiment: 12-week old C3H mice were SHAM or OVX operated (time −3). Three weeks after the ovariectomy treatment was started (time 0) with MV2 (1 µg/kg three times per week p.o.) or vehicle (veh., arachis oil) during 8 weeks. Calcium levels were determined just before the surgery (time −3), three weeks after the ovariectomy (time 0, start of treatment), four and eight weeks after treatment FIG. 11 shows data of the following experiment: 12-week old C3H mice were SHAM or OVX operated (time −3). Three weeks after the ovariectomy treatment was started (time 0) with MV2 (1 μg/kg three times per week p.o.) or vehicle (arachis oil) during 8 weeks. Body weight was evaluated in time.

DETAILED DESCRIPTION OF THE INVENTION

The terms "bone disorder" as used herein refers to disorders in which the bone calcium levels is abnormally low and/or bone resorption is abnormal, such as in osteoporosis, osteomalacia, Paget's disease, renal osteodystrophy, and disorders of the parathyroid function, or osteoarthritis.

The present invention addresses the following unmet medical needs, inter alia;
1) providing compounds and pharmaceutical compositions capable of effectively controlling, in particular preventing or treating bone disorders such as osteoporosis, without inducing elevated plasma calcium concentrations (hypercalcemia) and/or hypercalciuria.
2) providing compounds and pharmaceutical compositions capable of effectively controlling, in particular preventing or treating bone disorders such as but not limited to osteoporosis.

Methods for the preparation of vitamin $D_3$ analogues selected from the group consisting of:
(1R,3S)-5-((Z,2E)-3-((1S,3R)-3-((1S)-6,6,6-trifluoro-5-hydroxy-1-methyl-5-trifluoromethyl-3-hexynyl)-2,2,3-trimethylcyclopentyl)-2-propenylidene)-4-methylenecyclohexane-1,3-diol,
(1R,3S)-5-((Z,2E)-3-((1S,3R)-3-((1R)-6,6,6-trifluoro-5-hydroxy-1-methyl-5-trifluoromethyl-3-hexynyl)-2,2,3-trimethylcyclopentyl)-2-propenylidene)-4-methylenecyclohexane-1,3-diol,
(1R,3S)-5-((Z,2E)-3-((1S,3R)-3-((1R)-5-hydroxy-1,5-dimethyl-3-hexynyl)-2,2,3-trimethylcyclopentyl)-2-propenylidene)-4-methylenecyclohexane-1,3-diol,
(1R,3S)-5-((Z,2E)-3-((1S,3R)-3-((1S)-6,6,6-trifluoro-5-hydroxy-1-methyl-5-(trifluoromethyl)hexyl)-2,2,3-trimethylcyclopentyl)-2-propenylidene)-4-methylenecyclohexane-1,3-diol,
(1R,3S)-5-((Z,2E)-3-((1S,3R)-3-((1R)-6,6,6-trifluoro-5-hydroxy-1-methyl-5-(trifluoromethyl)hexyl)-2,2,3-trimethylcyclopentyl)-2-propenylidene)-4-methylenecyclohexane-1,3-diol,
(1R,3R)-5-((E)-3-((1S,3R)-3-((1R)-6,6,6-trifluoro-5-hydroxy-1-methyl-5-trifluoromethyl-3-hexynyl)-2,2,3-trimethylcyclopentyl)-2-propenylidene)cyclohexane-1,3-diol, and
(1R,3R)-5-((E)-3-((1S,3R)-3-((1S)-5-ethyl-5-hydroxy-1-methylheptyl)-2,2,3-trimethylcyclopentyl)-2-propenylidene)cyclohexane-1,3-diol, have been disclosed in details in Wu et al. (cited supra).

The above-mentioned novel individual vitamin $D_3$ analogues of the present invention, in particular (1R,3R)-5-{(E)-3-[(S)-3-((S)-4-hydroxy-1-(S)-methyl-5-methyl-hexyl)-2,2,3-trimethyl-cyclopentyl]-allylidene}-cyclohexane-1,3-diol and its diastereomer (1R,3R)-5-{(E)-3-[(S)-3-((R)-4-hydroxy-1-(S)-methyl-5-methyl-hexyl)-2,2,3-trimethyl-cyclopentyl]-allylidene}-cyclohexane-1,3-diol, (1R,3S)-5-((Z,2E)-3-((1S,3R)-3-((1S,4R)-4-hydroxy-1,5-dimethyl-hexyl)-2,2,3-trimethylcyclopentyl)-2-propenylidene)-4-methylenecyclohexane-1,3-diol and (1R,3S)-5-((Z,2E)-3-((1S,3R)-3-((1S,4S)-4-hydroxy-1,5-dimethylhexyl)-2,2,3-trimethylcyclopentyl)-2-propenylidene)-4-methylenecyclohexane-1,3-diol, can be prepared by synthesis routes as outlined herein below in the following schemes and examples. These routes produce only one isomer of the possible diastereomers. However, the manufacturer may wish, for reasons unrelated to the present invention, not to separate enantiomers or diastereomers at some point during said preparation.

The preparation of the vitamin $D_3$ analogues of this invention involves a step wherein the upper D-Ring scaffold of the vitamin $D_3$ molecule is coupled to the lower A-Ring portion via Lythgoe coupling, using knowledge taken for instance from *J. Chem. Soc., Perkin Trans.* (1978) 1:590 and ibid. 1290.

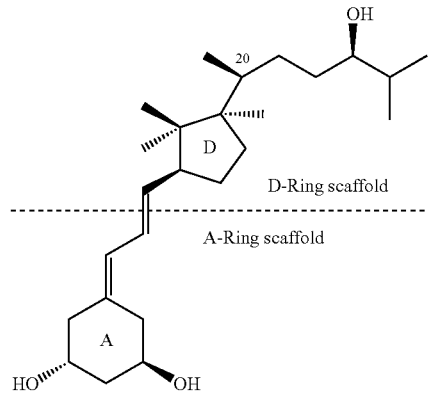

Preparation of the D-Ring Scaffold of the vitamin $D_3$ molecule may be effected, among other methods, according to the following scheme I (also illustrated in examples 1 to 3) outlining the preparation of 3-(tert-butyl-diphenyl-silanyloxymethyl)-1,2,2-trimethyl-cyclopentanecarbaldehyde (intermediate 4) from camphoric acid in three steps, exemplary but non limiting reaction conditions of each step being detailed herein below.

Scheme 1

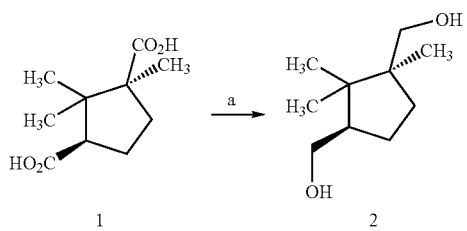

Reagents and conditions for step (a): LiAlH$_4$, solvent THF (tetrahydrofuran)-Et$_2$O (diethylether), about 20° C., 5 hours.

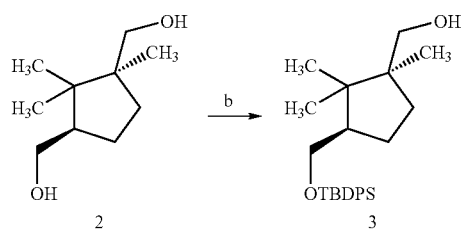

Reagents and conditions for step (b): TBDPSCl, imidazole, DMF (dimethylformamide), about 0° C. to 20° C., 5 hours.

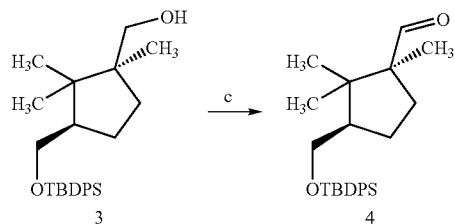

Reagents and conditions for step (c): (COCl)$_2$, solvents DMSO (dimethyl-sulfoxide) and CH$_2$Cl$_2$ (methylene chloride), at about −78° C., then Et$_3$N, −78° C. to 0° C.

A procedure for introducing a side-chain into the upper D-Ring portion of the vitamin D$_3$ molecule may be effected, among other methods, according to the following scheme II (also illustrated in example 4 to 17) outlining the preparation of 3-[4-(tert-butyl-diphenyl-silanyloxy)-1,5-dimethylhexyl]-2,2,3-trimethyl-cyclopentanecarbaldehyde (19) from intermediate (4) in thirteen steps, exemplary but non limiting reaction conditions of each step being detailed herein below.

Scheme II

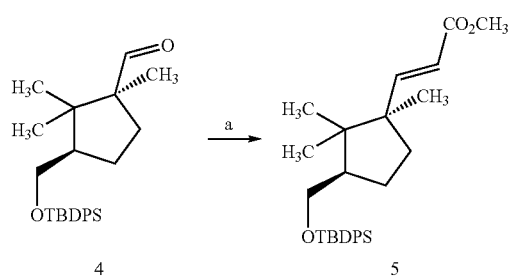

Reagents and conditions for step (a): (Et$_2$O)P(O)CH$_2$CO$_2$CH$_3$, NaH, THF, about 0° C., 3 hours.

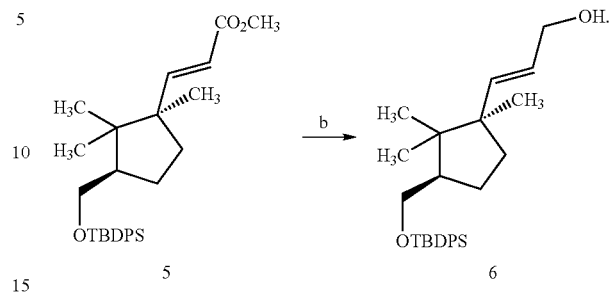

Reagents and conditions for step (b): diisobutylaluminium hydride (reducing agent), CH$_2$Cl$_2$, about −78° C. to −55° C., 4 hours.

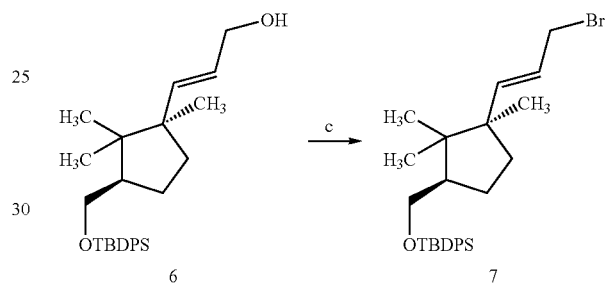

Reagents and conditions for step (c): CBr$_4$, PPh$_3$, CH$_2$Cl$_2$, about −60° C. to −35° C., 2 hours.

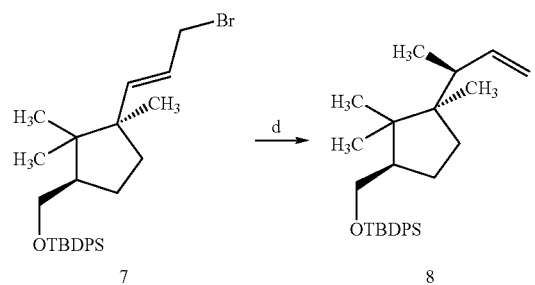

Reagents and conditions for step (d): CH$_3$SCuBr, CH$_3$Li, ZnCl$_2$, THF, Et$_2$O, about −78° C., 4 hours.

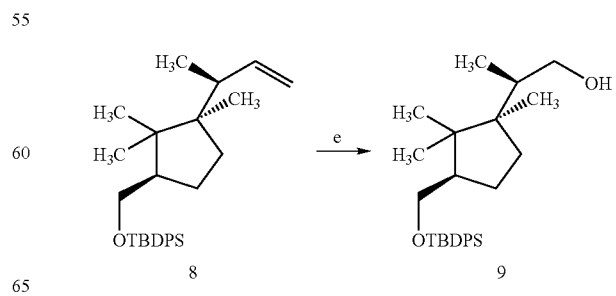

Reagents and conditions for step (e): O$_3$, NaBH$_4$, MeOH, CH$_2$Cl$_2$, hexane, pyridine, about −78° C., 3 hours.

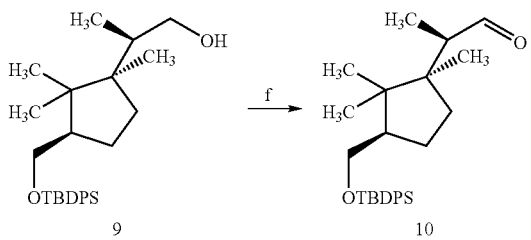

9    10

Reagents and conditions for step (f): (COCl)$_2$, DMSO, CH$_2$Cl$_2$, about −78° C., then Et$_3$N, about −78° C. to 0° C.

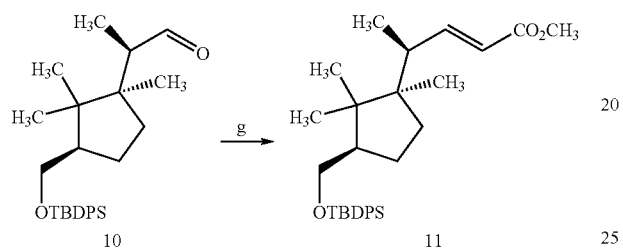

10    11

Reagents and conditions for step (g): (Et$_2$O)P(O)CH$_2$CO$_2$CH$_3$, NaH, THF, about 0° C., 1 hour.

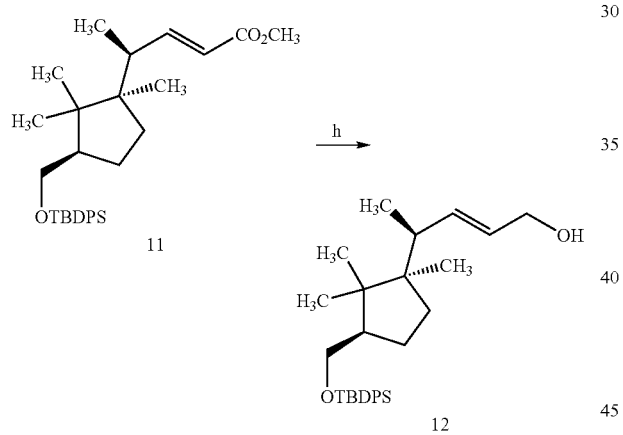

11

12

Reagents and conditions for step (h): diisobutylaluminium hydride (reducing agent), CH$_2$Cl$_2$, about −78° C. to −30° C., 3 hours.

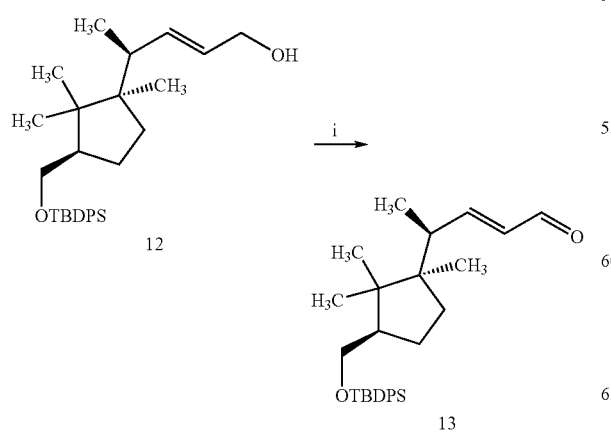

12

13

Reagents and conditions for step (i): (COCl)$_2$, DMSO, CH$_2$Cl$_2$, about −78° C.; Et$_3$N, about −78° C. to 0° C., 2 hours.

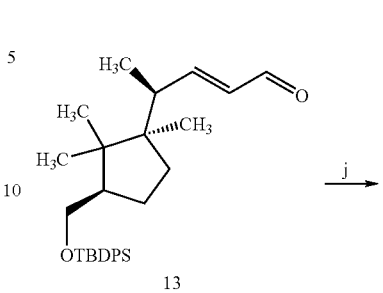

13

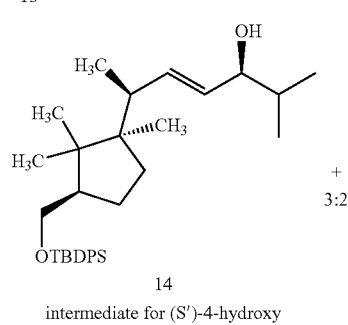

14
intermediate for (S′)-4-hydroxy

+

3:2

15
intermediate for (R)-4-hydroxy

Reagents and conditions for step (j) i-PrMgCl, diethyl ether (solvent), about −20° C. to 0° C., 2 hours.

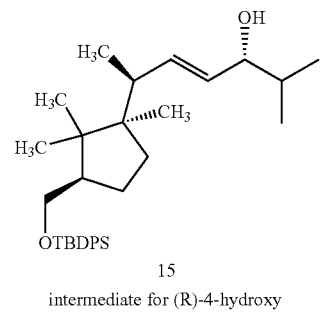

14

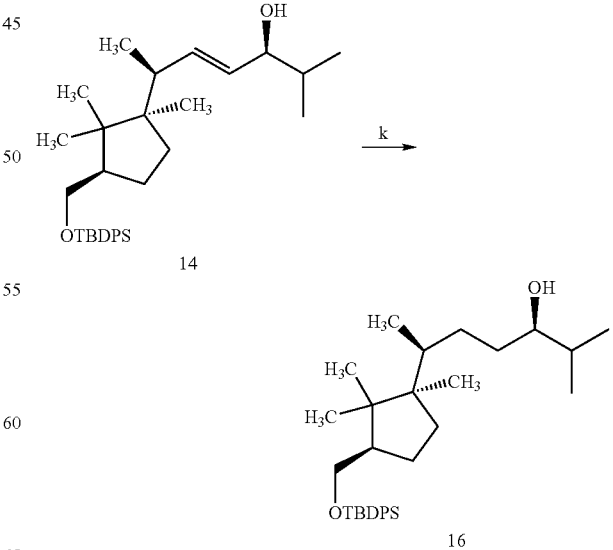

16

Reagents and conditions for step (k): H₂, Rh/Al₂O₃, ethyl acetate (solvent), about 20° C., 4 hours.

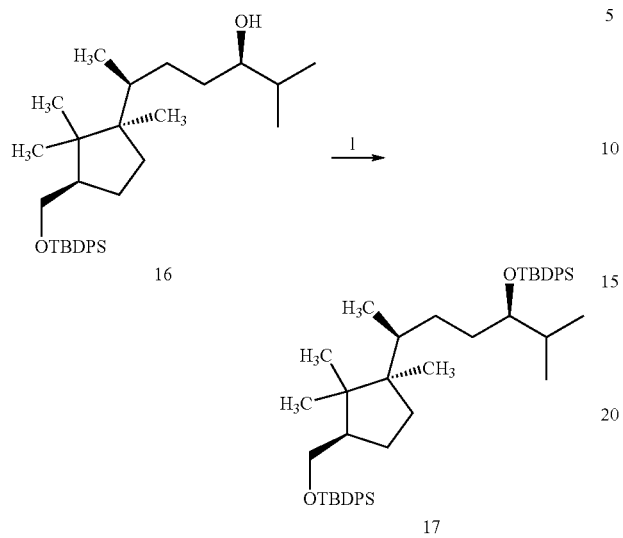

Reagents and conditions for step (l): TBDPSCI, imidazole, pyridine (solvent), about 20° C., 48 hours.

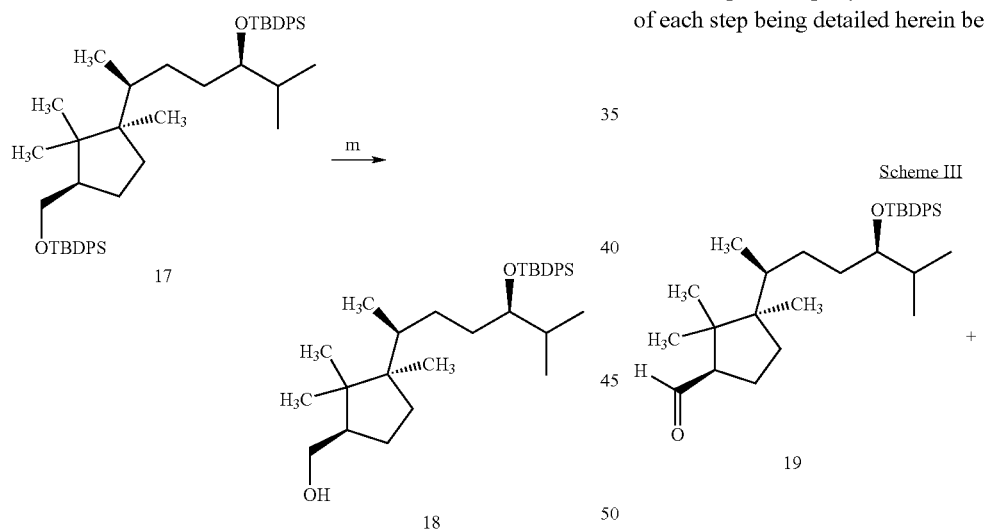

Reagents and conditions for step (m): TBAF, THF (solvent), about 20° C., 3 hours.

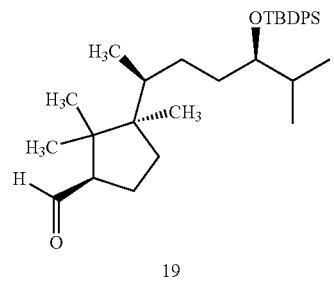

Reagents and conditions for step (n): (COCl)₂, DMSO, CH₂Cl₂, about −78° C.; Et₃N, about −78° C. to 0° C., 2 hours.

A procedure for coupling the upper D-Ring portion to the lower A-Ring section via the procedure of Perlman et al. in *Tetrahedron Lett.* (1991) 32:7663-7666 may be effected, among other methods, according to the following scheme III (also illustrated in examples 18 and 19) outlining the preparation of (1R,3R)-5-{(E)-3-[(S)-3-((S)-4-Hydroxy-1-(S)-methyl-5-methyl-hexyl)-2,2,3-trimethylcyclo-pentyl]-allylidene}-cyclohexane-1,3-diol (22) from intermediate (19) in two steps, exemplary but non limiting reaction conditions of each step being detailed herein below.

Scheme III

-continued

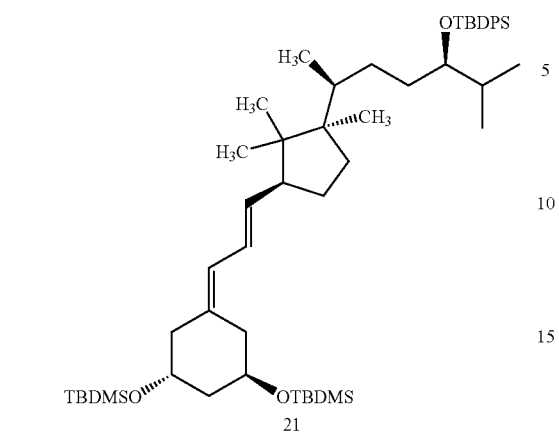

Reagents and conditions for step (a): n-BuLi, THF, about −78° C., 3 hours.

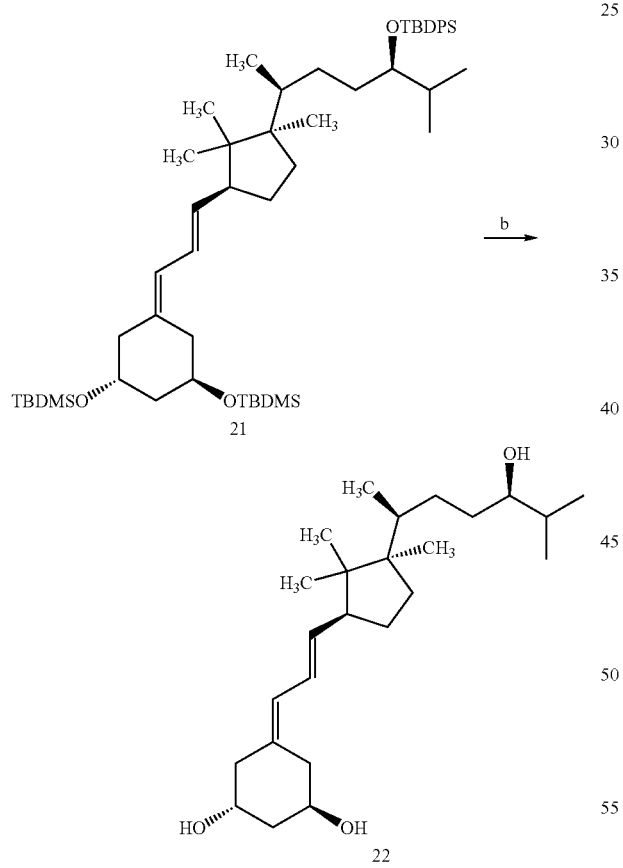

Reagents and conditions for step (b): n-BU$_4$NF, THF, about 20° C., 12 hours.

Other diastereomers of (1R,3R)-5-{(E)-3-[(S)-3-((S)-4-hydroxy-1-(S)-methyl-5-methyl-hexyl)-2,2,3-trimethyl-cyclopentyl]-allylidene}-cyclohexane-1,3-diol can be made similarly by using starting materials having a different stereochemistry for preparing alternative D-ring scaffolds according to the method of scheme 1. For example, in place of camphoric acid, starting materials having one of the following formulae:

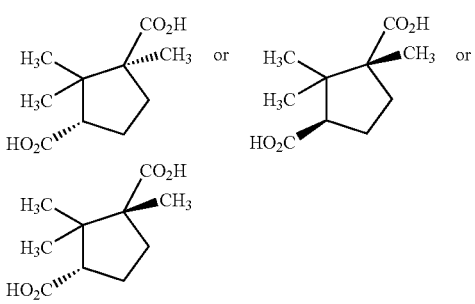

may be used alternatively in order to change the stereochemistry of one or more chiral centers of the intermediates and final compounds produced during the synthetic route.

An alternative procedure for introducing a side-chain into the upper D-Ring portion of the vitamin D$_3$ molecule may be effected, among other methods, according to the sequence of schemes illustrated in examples 20-26 and 29-31 outlining the preparation of intermediates of other vitamin D$_3$ molecules according to this invention. The upper D-Ring scaffolds thus obtained are then coupled to the lower A-Ring scaffold via a procedure similar to scheme III, as further illustrated in examples 27-28 and 32.

EXAMPLE 1

Preparation of (3-hydroxymethyl-2,2,3-trimethyl-cyclopentyl)-methanol (2)

To a solution of (1S,3R)-camphoric acid (1) (3.0 g, 14.8 mmol) in dry THF (40 mL) and dry Et$_2$O (30 mL) was added LiALH$_4$ (2.0 g, 52.6 mmol) and the reaction mixture was refluxed for 5 hours. The reaction was then quenched by the addition of Na$_2$SO$_4$.10H$_2$O (8.5 g) and the mixture stirred for 0.5 hour. H$_2$O (100 mL) was added and the aqueous layer extracted with CH$_2$Cl$_2$ (3×50 mL). The combined organic layers were dried over anhydrous MgSO$_4$ and the solvents concentrated in vacuo to a residue which was purified over silica (n-hexane/EtOAc, 6:4) to afford 2.39 g (95% yield) of the desired intermediate (2) as crystals which were characterized as follows:

R$_f$ (n-hexane/ethyl acetate, 1:1) 0.30;

optical rotation $[\alpha]_D^{rt}$ −56.6 (c=1, CHCl$_3$);

infrared (IR) spectrum (KBr film): absorption bands at 3269, 2964, 1369, 1092 and 1023 cm$^{-1}$;

proton nuclear magnetic resonance (hereinafter referred as $^1$H NMR) (500 MHz, CDCl$_3$): chemical shifts at 3.73 (1H, dd, J=9.2, 5.6 Hz), 3.58 (1H, d, J=10.7 Hz), 3.51 (1H, dd, J=9.2, 9.1 Hz), 3.46 (1H, d, J=10.7 Hz), 2.08 (1H, m), 1.95 (1H, m), 1.59 (1H, m), 1.21 (2H, br m), 1.01 (6H, s) and 0.79 (3H, s) ppm;

mass spectrum MS m/z(%) 154 (M$^+$-H$_2$O, 3), 139 (57), 123 (8), 109 (26), 81 (100) and 69 (88).

EXAMPLE 2

Preparation of [3-(tert-butyl-diphenyl-silanyloxymethyl)-1,2,2-trimethyl-cyclopentyl]-methanol (3)

To a solution of (3-hydroxymethyl-2,2,3-trimethyl-cyclopentyl)-methanol (2) (3.22 g, 18.67 mmol) and imidazole (1.54 g, 22.4 mmol) in DMF (100 mL) at 0° C. was added tert-butyl-diphenylsilyl chloride (5.95 mL, 22.4 mmol) over a period of 15 minutes. The reaction mixture was stirred at 0° C. for 0.5 hour and at 20° C. for 1 hour, then poured into $H_2O$ (300 mL) and $Et_2O$ (100 mL), and the aqueous layer was extracted with $Et_2O$ (3×50 mL). The combined organic layers were washed with brine (2×50 mL) and dried over anhydrous $MgSO_4$. The solvents were removed in vacuo and the residue was purified over silica (n-hexane/ethyl acetate, 8:2) to afford 6.68 g (87% yield) of the desired intermediate (3) as white crystals which were characterized as follows:

$R_f$ (n-hexane/ethyl acetate, 8:2) 0.28;

$[\alpha]_D^{rt}$ −20.3 (c=1, $CHCl_3$);

IR (KBr film) absorption bands at 3374, 2959, 1472, 1389, 1111, 1066, 739 and 702 $cm^{-1}$;

$^1$H NMR (500 MHz, $CDCl_3$) chemical shifts at 7.68 (4H, dd, J=7.8, 1.5 Hz), 7.40 (6H, m), 3.70 (1H, dd, J=10.1, 6.4 Hz), 3.54 (1H, dd, J=10.1, 7.4 Hz), 3.53 (1H, d, J=10.6), 3.45 (1H, d, J=10.6 Hz), 2.14 (1H, m), 1.88 (1H, m), 1.55 (1H, m), 1.36-1.22 (2H, m), 1.04 (9H, s), 0.99 (3H, s), 0.96 (3H, s) and 0.75 (3H, s) ppm;

MS m/z (%) 410 ($M^+$, 1), 379 (3), 229 (15), 199 (79), 137 (100) and 95 (47).

EXAMPLE 3

Preparation of 3-(tert-butyl-diphenyl-silanvloxymethyl)-1,2,2-trimethyl-cyclo-pentanecarbaldehyde (4)

To a solution of oxalyl chloride (0.977 mL, 11.2 mmol) in dry $CH_2Cl_2$ (20 mL) at −78° C. was added dropwise DMSO (1.19 mL, 16.8 mmol) in dry $CH_2Cl_2$ (2.0 mL) over a period of 10 minutes and the mixture was stirred at −78° C. for 15 minutes. A solution of [3-(tert-butyl-diphenyl-silanyloxymethyl)-1,2,2-trimethyl-cyclopentyl]-methanol (2) (2.30 g, 5.6 mmol) in dry $CH_2Cl_2$ (6.0 mL) was added dropwise at −78° C. over a period of 30 minutes and the reaction mixture was stirred at −78° C. for 30 minutes. Triethylamine (3.9 mL, 28.0 mmol) was added dropwise at −78° C. over a period of 10 minutes and the reaction mixture was stirred at −78° C. for 1 hour. The temperature of the mixture is allowed to rise to −10° C. over a period of 3.5 hours and cold $H_2O$ (60 mL) was added. The organic layer was separated, the aqueous layer was extracted with $Et_2O$ (3×60 mL) and the combined organic layers were dried over anhydrous $MgSO_4$. The solvents were removed in vacuo and the residue was purified over silica (n-hexane/ ethyl acetate, 98:2) to afford 2.21 g (97% yield) of the desired product (4) as a viscous oil which was characterized as follows:

$R_f$ (n-hexane/ethyl acetate, 98:2) 0.22;

$[\alpha]_D^{rt}$ −25.86 (c=1, $CHCl_3$);

IR (KBr film) 2953, 1722, 1659, 1112, 1062, 740 and 702 $cm^{-1}$;

$^1$H NMR (500 MHz, $CDCl_3$) chemical shifts at 9.53 (1H, s), 7.66 (4H, dd, J=8.0, 1.5 Hz), 7.41 (6H, m), 3.69 (1H, dd, J=10.3, 6.8 Hz), 3.57 (1H, dd, J=10.3, 6.9 Hz), 2.29 (1H, m), 2.14 (1H, m), 1.91 (1H, m), 1.45-1.20 (2H, m), 1.06 (3H, s), 1.05 (12H, s) and 0.85 (3H, s) ppm;

MS m/z (%) 407 ($M^+$, 1), 289 (51), 199 (61), 135 (26) and 123 (100).

EXAMPLE 4

Preparation of 3-[3-(tert-butyl-diphenyl-silanyloxymethyl)-1,2,2-trimethyl-cyclopentyl]-acrylic acid methyl ester (5)

To a suspension of NaH (60% dispersion in petroleum ether; 1.47 g, 36.7 mmole) in dry THF (50 mL) at 0° C. was added dropwise diethylmethoxy-carbonylmethylphosphonate (6.88 mL, 36.71 mmole) over a period of 10 minutes. The solution was stirred at 0° C. for 35 minutes (color change to pale yellow) and 3-(tert-butyldiphenylsilanyloxymethyl)-1,2,2-trimethyl-cyclo-pentanecarbaldehyde (4) (10.0 g, 24.47 mmole) in dry THF (20 mL) was added dropwise over a period of 20 minutes. The reaction mixture was stirred at 0° C. for 3 hours and poured into cold water (500 mL). The aqueous layer was extracted with $Et_2O$ (4×100 mL) and the combined organic layers were dried over anhydrous $MgSO_4$. The solvent was removed in vacuo and the residue was purified over a short column of silica (n-hexane/ethyl acetate, 9:1) and further purified over silica (n-hexane/ethyl acetate, 95:5) to afford 11.15 g (98% yield) of the desired intermediate (5) as a colorless oil which was characterized as follows:

$R_f$ (n-hexane/EtOAc, 95:5) 0.27;

IR (KBr film) absorption bands at 2961, 1725, 1428, 1399, 1172, 1111, 740 and 705 $cm^{-1}$;

$^1$H NMR (500 MHz, $CDCl_3$) chemical shifts at 7.67 (4H, dd, J=8.0, 1.5 Hz), 7.40 (6H, m), 7.04 (1H, d, J=16.0 Hz), 5.72 (1H, d, J=16.0 Hz), 3.72 (3H, s), 3.69 (1H, dd, J=9.6, 6.9 Hz), 3.56 (1H, dd, J=9.6, 7.2 Hz), 2.15 (1H, m), 1.90 (1H, m), 1.04 (9H, s), 0.99 (3H, s), 0.94 (3H, s) and 0.68 (3H, s) ppm;

MS m/z (%) 465 ($M^+$, 1), 407 (100), 289 (14), 199 (75), 135 (95) and 77 (35).

EXAMPLE 5

Preparation of 3-[3-(tert-butyl-diphenyl-silanyloxymethyl)-1,2,2-trimethyl-cyclopentyl]-prop-2-en-1-ol (6)

Intermediate (5) (11.12 g, 23.92 mmol) in $CH_2Cl_2$ (150 mL) at −78° C. was added dropwise diisobutylaluminium hydride (1.5 M solution in toluene; 63.8 mL, 95.67 mmol) over a period of 30 minutes. After stirring at −78° C. for 2 hours, the reaction mixture was allowed to warm to −55° C. over a period of 2 hours and the reaction was quenched by the addition of a 2 N K-Na-tartrate solution (100 mL). $H_2O$ (400 mL) was added and the aqueous layer was extracted with $Et_2O$ (4×150 mL). The combined organic layers were dried over anhydrous $MgSO_4$, the solvent removed in vacuo and the resulting residue was purified over silica (n-hexane/ethyl acetate, 85:15) to afford 10.34 g (99% yield) of the desired intermediate (6) as a colourless oil which was characterized as follows:

$R_f$ (n-hexane/EtOAc, 8:2) 0.32;

IR (KBr film) absorption bands at 3342, 2961, 2858, 1427, 1389, 1111, 739 and 702 $cm^{-1}$;

$^1$H NMR (500 MHz, $CDCl_3$) chemical shifts at 7.67 (4H, dd, J=8.0, 1.5 Hz), 7.40 (6H, br m), 5.73 (1H, d, J=15.7 Hz), 5.54 (1H, dt, J=15.7, 5.7 Hz), 4.12 (2H, dd, J=5.7, 5.3 Hz), 3.69 (1H, dd, J=10.5, 6.8 Hz), 3.55 (1H, dd, J=10.5, 7.2 Hz), 1.04 (9H, s), 0.95 (3H, s), 0.89 (3H, s) and 0.64 (3H, s) ppm; and MS m/z (%) 436 (M$^+$, 1), 379 (3), 229 (12), 199 (100), 163 (48), 107 (68).

EXAMPLE 6

Preparation of [3-(3-bromo-propenyl)-2,2,3-trimethyl-cyclopentyl-methoxy]-tert-butyl-diphenyl-silane (7)

To a solution of CBr$_4$ (98%; 12.02 g, 35.52 mmol) and triphenylphosphine (98%; 9.51 g, 35.52 mmol) in CH$_2$Cl$_2$ (120 mL) at −60° C. was added dropwise intermediate (6) (10.34 g, 23.67 mmol) in CH$_2$Cl$_2$ (30 mL) over a period of 20 minutes and the reaction mixture was allowed to warm up to −35° C. over a period of 2 hours. After removal of the solvent under reduced pressure, n-hexane (300 mL) was added. The precipitate was filtered off and the filtrate was concentrated in vacuo and the resulting residue was purified over silica (n-hexane/EtOAc, 99:1) to afford 11.48 g (97% yield) of the desired intermediate (7) as a colorless oil which was characterized as follows:

R$_f$ (n-hexane/EtOAc, 99:1) 0.33;

IR (KBr film) absorption bands at 2961, 2858, 1423, 1389, 1112, 1072, 740 and 702 cm$^{-1}$;

$^1$H NMR (500 MHz, CDCl$_3$) chemical shifts at 7.67 (4H, dd, J=7.8, 1.4 Hz), 7.40 (6H, br m), 5.81 (1H, d, J=15.4 Hz), 5.59 (1H, dt, J=15.4, 7.7 Hz), 3.98 (2H, d, J=7.7 Hz), 3.68 (1H, dd, J=10.1, 6.9 Hz), 3.55 (1H, dd, J=10.1, 7.3 Hz), 1.04 (9H, s), 0.95 (3H, s), 0.90 (3H, s), 0.65 (3H, s) ppm; and MS m/z (%) 499 (M$^+$, 1), 419 (3), 363 (5), 261 (18), 199 (64), 163 (94) and 107 (100).

EXAMPLE 7

Preparation of tert-butyl-diphenyl-[2,2,3-trimethyl-3-(1-methyl-allyl)-cyclopentyl-methoxy]-silane (8)

To Me$_2$S.CuBr (dried twice by azeotropic distillation with toluene; 5.04 g, 24.02 mmol) in dry THF (40 mL) at −78° C. was added dropwise CH$_3$Li (1.4 M solution in Et$_2$O; 34.30 mL, 48.04 mmol) over a period of 15 minutes. Stirring of the suspension at −50 to −60° C. for 30 minutes resulted in a color change to yellow, after which a solution of freshly fused ZnCl$_2$ (98%; 3.49 g, 25.11 mmol) in dry THF (25 mL) was added dropwise at −50° C. to −60° C. over a period of 20 minutes. The reaction mixture was then stirred at −55° C. for 1 hour, the suspension is cooled to −78° C. and intermediate (7), (5.74 g, 11.49 mmol) in dry THF (10 mL) was added dropwise over a period of 30 minutes. The reaction mixture was stirred at −78° C. for 1 hour and then allowed to warm up to −40° C. over a period of 4 hours. After stirring at room temperature for 20 minutes, the mixture was poured into a saturated NH$_4$Cl solution containing 10% of NH$_4$OH (200 mL). The solution was stirred an additional 30 minutes then the aqueous layer was extracted with n-hexane/diethyl ether 95:5 (4×100 mL). The combined organic layers were dried over anhydrous MgSO$_4$, the solvent removed under reduced pressure and the crude residue was purified over silica (n-hexane) to afford 3.96 g (79% yield) of the desired intermediate (8) as a colorless oil which was characterized as follows:

R$_f$ (n-hexane) 0.26;

[□]$_D^{rt}$+41.08 (c=0.72, CHCl$_3$);

IR (KBr film) absorption bands at 2962, 1428, 1377, 1112, 1070, 824 and 701 cm$^{-1}$;

$^1$H NMR (500 MHz, CDCl$_3$) chemical shifts at 7.67 (4H, br m), 7.39 (6H, br m), 5.88 (1H, ddd, J=17.5, 10.2, 9.7 Hz), 4.93 (1H, dd, J=17.5, 2.1 Hz), 4.91 (1H, dd, J=10.2, 2.1 Hz), 3.69 (1H, dd, J=9.8, 6.1 Hz), 3.51 (1H, dd, J=9.8, 7.7 Hz), 1.03 (9H, s), 0.90 (3H, s), 0.90 (3H, d, J=5.1 Hz), 0.84 (3H, s) and 0.75 (3H, s) ppm;

MS m/z (%) 434 (M$^+$, 1), 377 (40), 307 (22), 199 (100), 181 (15), 135 (40) and 107 (26).

EXAMPLE 8

Preparation of 2-[3-tert-butyl-diphenyl-silanyloxymethyl)-1,2,2-trimethyl-cyclo-pentyl]-propan-1-ol (9)

Through a solution of intermediate (8) (4.00 g, 9.2 mmol) in a mixture of MeOH (40 mL), CH$_2$Cl$_2$ (40 mL), n-hexane (40 mL) and pyridine (1.3 mL) at −78° C. was bubbled ozone for 3 hours. NaBH$_4$ (4.0 g) was then added in four portions at −78° C. to −20° C. over a period of 3 hours. The reaction mixture was stirred at room temperature for 30 minutes, after which water (400 mL) was added and the aqueous layer was extracted with Et$_2$O (4×50 mL). The combined organic layers were washed with a 1 N HCl solution (10 mL) and brine (2×50 mL), dried over anhydrous MgSO$_4$, concentrated under reduced pressure and the resulting residue purified by HPLC over silica (n-hexane/ethyl acetate, 85:15) to afford 3.36 g (83% yield) of the desired intermediate (9) as a colourless oil which was characterized as follows:

R$_f$ (n-hexane/EtOAc, 8:2) 0.41;

IR (KBr film) absorption bands at 3370, 2963, 1428, 1379, 1112, 824 and 702 cm$^{-1}$;

$^1$H NMR (500 MHz, CDCl$_3$) chemical shifts at 7.67 (4H, dd, J=7.8, 1.4 Hz), 7.40 (6H, br m), 3.94 (1H, dd, J=10.2, 3.6 Hz), 3.70 (1H, dd, J=10.0, 6.0 Hz), 3.52 (1H, dd, J=10.0, 7.7 Hz), 3.30 (1H, dd, J=10.2, 10.1 Hz), 2.15 (1H, br m), 1.04 (9H, s), 0.97 (3H, s), 0.96 (3H, d, J=7.8 Hz), 0.81 (3H, s) and 0.79 (3H, s) ppm;

MS m/z (%) 438 (M$^+$, 1), 229 (12), 199 (85), 135 (26), 109 (100).

EXAMPLE 9

Preparation of 2-[3-tert-butyl-diphenyl-silanyloxymethyl)-1,2,2-trimethyl-cyclo-pentyl]-propionaldehyde (10)

To a solution of oxalyl chloride (1.193 mL, 13.68 mmol) in dry CH$_2$Cl$_2$ (30 mL) at −78° C. was added dropwise DMSO (1.619 mL, 22.79 mmol) in dry CH$_2$Cl$_2$ (4.0 mL) over a period of 10 minutes and the mixture was then stirred at −78° C. for 15 minutes. A solution of intermediate (9) (2.0 g, 4.56 mmol) in dry CH$_2$Cl$_2$ (10 mL) was then added dropwise at −78° C. over a period of 30 minutes and the reaction mixture stirred at −78° C. for 30 minutes. Triethylamine (4.448 mL, 31.91 mmol) was then added dropwise at −78° C. over a period of 10 minutes and the reaction mixture stirred at −78° C. for 1 hour. The temperature of the mixture was allowed to rise to −10° C. over a period of 3.5 hour, after which cold water (200 mL) was added. The organic layer was separated, the aqueous layer was extracted with diethyl ether (3×200 mL) and the combined organic layers were dried over anhydrous MgSO$_4$, the solvent removed in vacuo and the resulting residue was purified over silica (n-hexane/ethyl acetate, 97:3)

to afford 1.912 g (96% yield) of the desired intermediate (10) as a colourless oil which was characterized as follows:

$R_f$ (n-hexane/EtOAc, 95:5) 0.37;
$[\alpha]_D^{rt}$ -58.56 (c=1.11, CHCl$_3$);
IR (KBr film) absorption bands at 2960, 1718, 1390, 1111, 824 and 702 cm$^{-1}$;
$^1$H NMR (500 MHz, CDCl$_3$) chemical shifts at 9.81 (1H, d, J=4.6 Hz), 7.66 (4H, m), 7.39 (6H, m), 3.69 (1H, dd, J=10.1, 6.4 Hz), 3.53 (1H, dd, J=10.1, 7.4 Hz), 2.54 (1H, qd, J=6.9, 4.6 Hz), 2.16 (1H, m), 1.04 (9 H, s), 1.04 (1H, d, J=6.8 Hz), 1.02 (3H, s), 0.91 (3H, s) and 0.84 (3H, s) ppm; and
MS m/z (%) 436 (M$^+$, 1), 379 (13), 239 (24), 199 (61), 123 (100) and 87 (57).

EXAMPLE 10

Preparation of (2E,4S) methyl 4-((1R,3R)-3-(tert-butyldiphenyl-silyloxymethyl)-1,2,2-trimethylcyclopentyl)pent-2-enoate (11)

To a suspension of NaH (60% dispersion in petroleum ether; 0.33 g, 8.234 mmol) in dry THF (10.0 mL) was added dropwise (Et$_2$O)P(O)CH$_2$CO$_2$Me (1.54 mL, 8.234 mmol) at 0° C. over a period of 10 minutes. The solution was stirred at 0° C. for 25 minutes and intermediate (10) (0.87 g, 1.992 mmol) in dry THF (4.0 mL) was added dropwise over a period of 15 minutes. The reaction mixture was stirred at 0° C. for 1 hour and then poured into a mixture of cold water (100 mL) and diethyl ether (50 mL). The aqueous layer was extracted with diethyl ether (3×25 mL) and the combined organic layers were dried over anhydrous MgSO$_4$, the solvent was removed under reduced pressure and the residue was purified over silica (n-hexane/EtOAc, 9:1) to afford 0.9156 g (93% yield) of the desired intermediate (11) as a viscous oil which was characterized as follows:

$R_f$ (isooctane/EtOAc, 97:3) 0.40;
IR (KBr film) absorption bands at 2930, 2858, 1726, 1651, 1428, 1284, 1194, 1112, 824 and 706 cm$^{-1}$;
$^1$H NMR (500 MHz, CDCl$_3$) chemical shifts at 7.66 (4H, dd, J=7.9, 1.4 Hz), 7.39 (6H, m), 7.08 (1H, dd, J=15.7, 9.8 Hz), 5.76 (1H, d, J=15.7 Hz), 3.72 (3H, s), 3.68 (1H, dd, J=10.1, 6.4 Hz), 3.51 (1H, dd, J=10.1, 7.4 Hz), 2.50 (1H, m), 2.10 (1H, m), 1.80 (1H, m), 1.03 (9H, s), 0.96 (3 H, d, J=7.0 Hz), 0.89 (3H, s), 0.85 (3H, s) and 0.73 (3H, s) ppm;
MS m/z (%) 492 (M$^+$, 1), 449 (4), 435 (50), 407 (7), 32 (17), 243 (29), 199 (100), 183 (38), 135 (60), 81 (33) and 41 (44).

EXAMPLE 11

Preparation of (2E,4S)-4-((1R,3R)-3-(tert-butyl-diphenylsilyloxy-methyl)-1,2,2-trimethylcyclopentyl)pent-2-en-1-ol (12)

To a solution of intermediate (11) (0.914 g, 1.91 mmol) in dry CH$_2$Cl$_2$ (12.0 mL) was added dropwise diisobutylaluminium hydride (1.5 M solution in toluene; 7.6 mL, 11.455 mmol) at −78° C. The reaction mixture was stirred at −78° C. for 1 hour and then the temperature was allowed to rise to −30° C. over a period of 2 hours. A 2N K-Na-tartrate solution (100 mL) was slowly added at −30° C. and the mixture was stirred an additional 3 hours. The aqueous layer was extracted with isooctane/ethyl acetate 7:3 (4×30 mL) and the combined organic layers were dried over anhydrous MgSO$_4$, the solvent removed in vacuo and the residue was purified over silica (isooctane/ethyl acetata, 89:11) to afford 0.822 g (93% yield) of the desired intermediate (12) which was characterized as follows:

$R_f$ (isooctane/EtOAc, 85:15) 0.27;
IR (KBr film) absorption bands at 3332, 2961, 1378, 1111, 824 and 701 cm$^{-1}$;
$^1$H NMR (500 MHz, CDCl$_3$) chemical shifts at 7.66 (4H, dd, J=7.7, 1.3 Hz), 7.39 (6H, m), 5.75 (1H, dd, J=15.4, 9.3 Hz), 4.09 (2H, t, J=5.7 Hz), 3.68 (1H, dd, J=11.0, 6.2 Hz), 3.51 (1H, dd, J=10.5, 7.5 Hz), 2.36 (1H, m), 2.10 (1H, m), 1.81 (1H, m), 1.03 (9H, s), 0.91 (3H, d, J=6.8 Hz), 0.88 (3H, s), 0.85 (3H, s) and 0.75 (3H, s) ppm;
MS m/z (%) 464 (M$^+$, 1), 435 (2), 379 (5), 229 (5), 199 (100), 183 (8), 135 (44), 109 (34), 41 (32).

EXAMPLE 12

Preparation of (2E,4S)-4-((1R,3R)-3-(tert-butyl-diphenylsilyloxy-methyl)-1,2,2-trimethylcyclopentyl)pent-2-enal (13)

To a solution of oxalyl chloride (0.6377 mL, 7.31 mmol) in dry CH$_2$Cl$_2$ (15.0 mL) was added dropwise DMSO (0.7786 mL, 10.96 mmol) at −78° C. over a period of 10 minutes and the mixture was stirred at −78° C. for 15 minutes. A solution of intermediate (12) (0.820 g, 1.83 mmol) in dry CH$_2$Cl$_2$ (5.0 mL) was then added dropwise at −78° C. over a period of 30 minutes and the reaction mixture was stirred at −78° C. for 30 minutes. Triethylamine (2.04 mL, 14.6 mmol) was added dropwise at −78° C. over a period of 10 minutes and the reaction mixture was stirred at −78° C. for 1 hour. The temperature of the mixture was allowed to rise to −10° C. over a period of 3.5 hours and then H$_2$O (50 mL) was added. The organic layer was separated, the aqueous layer was extracted with diethyl ether (3×20 mL), the combined organic layers were dried over anhydrous MgSO$_4$, and the solvent was removed under reduced pressure and the resulting residue was purified over silica (n-hexane/EtOAc, 97:3) to afford 0.776 g (92% yield) of the desired intermediate (13) which was characterized as follows:

$R_f$ (isooctane/ethyl acetate, 97:3) 0.16;
IR (KBr film) absorption bands at 2929, 1694, 1380, 1112, 824 and 702 cm$^{-1}$;
$^1$H NMR (500 MHz, CDCl$_3$) chemical shifts at 9.52 (1H, d, J=6.9 Hz), 7.66 (4H, dd, J=7.7, 1.3 Hz), 7.39 (6H, m), 6.96 (1H, dd, J=15.7, 9.6 Hz), 6.08 (1H, dd, J=15.7, 7.9 Hz), 3.68 (1H, dd, J=10.0, 6.4 Hz), 3.52 (1H, dd, J=10.0, 7.3 Hz), 2.63 (1H, m), 2.10 (1H, m), 1.82 (1H, m), 1.03 (9H, s), 1.01 (3H, d, J=6.9 Hz), 0.92 (3H, s), 0.86 (3H, s) and 0.85 (3H, s) ppm; and
MS m/z (%) 462 (M$^+$, 1), 405 (25), 327, (5), 265 (10), 199 (100), 183 (27), 135 (56), 57 (50), 41 (54).

EXAMPLE 13

Preparation of (3S,4E,6S)-6-((1R,3R)-3-(tert-butyl-diphenylsilyl-oxymethyl)-1,2,2-trimethylcyclopentyl)-2-methylhept-4-en-3-ol (14) and (3R,4E,6S)-6-((1R,3R)-3-(tert-butyldiphenylsilyloxymethyl)-1,2,2-trimethyl-cyclopentyl)-2-methylhept-4-en-3-ol (15)

To a solution of intermediate (13) (0.300 g, 0.672 mmol) in dry diethyl ether (4.0 mL) was added dropwise isopropyl magnesium chloride (2 M solution in diethyl ether, 1.68 mL, 3.36 mmol) at −20° C. The reaction mixture was stirred at −20° C. for 0.5 hour and then the temperature was allowed to rise to 0° C. over a period of 2 hours. The reaction was then quenched by the addition of a 10% HCl solution to pH=6 and water (20 mL) was added. The aqueous layer was extracted with diethyl ether (3×30 mL) and the combined organic layers were dried over anhydrous MgSO$_4$, the solvent removed under reduced pressure and the 3:2 mixture of alcohols was separated by HPLC over silica (isooctane/ethyl acetate, 95:5) to give the alcohol shown in Scheme II as intermediate 14 (0.150 g) and the corresponding isomer alcohol shown in Scheme II as intermediate 15 (0.101 g) (85% combined yield). Non-reacted starting material (13) was also recovered (0.031 g). Intermediate 14 was identified by the following data:

$R_f$ (isooctane/ethyl acetate, 9:1) 0.24;

IR (KBr film) absorption bands at 3391, 2960, 1471, 1428, 1378, 1112, 1069, 1008, 976, 824 and 702 cm$^{-1}$;

$^1$H NMR (500 MHz, CDCl$_3$) chemical shifts at 7.67 (4H, dd, J=7.7, 1.2 Hz), 7.39 (6H, m), 5.72 (1H, dd, J=15.4, 8.9 Hz), 5.39 (1H, dd, J=15.4, 7.3 Hz), 3.78 (1H, m), 3.69 (1H, dd, J=10.0, 6.1 Hz), 3.51 (1H, dd, J=10.0, 7.6 Hz), 2.35 (1H, m), 2.10 (1H, m), 1.87 (1H, m), 1.03 (9H, s), 0.93 (6H, d, J=6.7 Hz), 0.89 (3H, s), 0.87 (3H, d, J=6.8 Hz), 0.84 (3H, s) and 0.77 (3H,s) ppm;

MS m/z (%) 506 (M$^+$, 1), 339 (4), 199 (100), 183 (13), 123 (62), 109 (39), 57 (38) and 43 (44).

Intermediate 15 was identified by the following data:

$R_f$ (isooctane/ethyl acetate, 9:1) 0.19;

IR (KBr film) absorption bands at 3386, 2962, 1472, 1428, 1378, 1112, 1065, 976, 824, 739 and 702 cm$^{-1}$;

$^1$H NMR (500 MHz, CDCl$_3$) chemical shifts at 7.67 (4H, d, J=6.7 Hz), 7.39 (6H, m), 5.74 (1H, dd, J=15.4, 9.2 Hz), 5.42 (1H, dd, J=15.4, 7.3 Hz), 3.81 (1H, dd, J=6.6, 6.6 Hz), 3.69 (1H, dd, J=10.0, 6.0 Hz), 3.51 (1H, dd, J=10.0, 7.7 Hz), 2.33 (1H, m), 2.10 (1H, m), 1.83 (1H, m), 1.72 (1H, m), 1.03 (9H, s), 0.92 (3H, d, J=6.8 Hz), 0.91 (3H, d, J=6.8 Hz), 0.89 (3H, d, J=6.7 Hz), 0.87 (3H, s), 0.85 (3H, s) and 0.74 (3H, s) ppm;

MS m/z (%) 506 (M$^+$, 1), 449 (2), 431 (2), 379 (3), 229 (12), 199 (100), 183 (13), 123 (62), 109 (40), 57 (44) and 43 (50).

EXAMPLE 14

Preparation of (3R,6S)-6-((1R,3R)-3-(tert-butyl-diphenylsilyloxy-methyl)-1,2,2-trimethylcyclopentyl)-2-methylheptan-3-ol (16)

A mixture of intermediate (14) (0.055 g, 0.1123 mmol) and Rh/Al$_2$O$_3$ (5% by weight; 0.02 g) in ethyl acetate (dried over 4 Å molecular sieves; 1.5 mL) was placed under H$_2$ atmosphere and vigorously stirred at room temperature for 4 hours. The reaction mixture was passed through a short column of silica (ethyl acetate) and the solvent was evaporated under reduced pressure. The resulting residue was purified by HPLC over silica (isooctane/ethyl acetate, 9:1) to afford 0.046 mg (83% yield) of the desired intermediate (16) which was characterized as follows:

$R_f$ (isooctane/EtOAc, 9:1) 0.24;

IR (KBr film) absorption bands at 3383, 2956, 1463, 1372, 1260, 1105, 1057, 804, 699 and 609 cm$^{-1}$;

$^1$H NMR (500 MHz, CDCl$_3$) chemical shifts at 7.67 (4H, dd, J=7.7, 1.5 Hz), 7.39 (6H, m), 3.71 (1H, dd, J=10.0, 5.9 Hz), 3.51 (1H, dd, J=10.0, 7.7 Hz), 3.31 (1H, m), 2.10 (1H, m), 1.03 (9H, s), 1.02 (3H, d, J=6.6 Hz), 0.92 (3H, d, J=6.8 Hz), 0.89 (3H, d, J=6.6 Hz), 0.80 (6H, s) and 0.73 (3H, s) ppm; and MS m/z (%) 508 (M$^+$, 1), 451 (2), 199 (100), 183 (18), 123 (50), 109 (77), 69 (74), 57 (57) and 43 (42).

EXAMPLE 15

Preparation of {6-[3-(tert-butyl-diphenyl-silanyloxymethyl)-1,2,2-trimethyl-cyclo-pentyl]-2-methyl-heptan-3-yl}-tert-butyl-diphenyl-silane (17)

To a solution of intermediate (16) (0.045 g, 0.088 mmol) and imidazole (0.0252 g, 0.366 mmol) in dry pyridine (1 mL) was added tert-butyl-diphenylsilyl chloride (97 µL, 0.366 mmol) at 20° C. and the reaction mixture was stirred for 48 hours. Water (30 mL) and diethyl ether (30 mL) were added and the mixture was neutralized to pH=6 using a 1 N hydrogen chloride solution. The aqueous layer was extracted with diethyl ether and the combined organic layers were dried over anhydrous MgSO$_4$. The solvent was removed under reduced pressure and the residue was purified over silica (isooctane/ethyl acetate, 98:2) and then used directly in the next step.

EXAMPLE 16

Preparation of (1R,3R)-(3-((1S,4R)-4-(tert-butyl-diphenylsilyloxy-methyl)-1,5-dimethylhexyl)-2,2,3-trimethylcyclopentyl)methanol (18)

To a solution of intermediate (17) in THF (1.0 mL) was added tetrabutyl-ammonium fluoride (1 M solution in THF; 0.137 mL, 0.137 mmol) and the reaction mixture was stirred at room temperature for 3 hours. The mixture was then passed through a short pad of silica gel (isooctane/ethyl acetate, 7:3) and the crude product obtained was purified by HPLC over silica (isooctane/EtOAc, 87:13) to afford 0.024 g (53% yield over the two steps) of the desired intermediate (18) as a viscous oil which was characterized as follows:

$R_f$ (isooctane/EtOAc, 87:13) 0.14;

IR (KBr film) absorption bands at 3384, 2961, 1653, 1558, 1457, 1420, 1380, 1111, 1042 and 702 cm$^{-1}$;

$^1$H NMR (500 MHz, CDCl$_3$) chemical shifts at 7.68 (4H, m), 7.38 (6H, m), 3.69 (1H, m), 3.52 (1H, m), 3.43 (1H, m), 1.98 (1H, m), 1.81 (1H, m), 1.70 (1H, m), 1.04 (9H, s), 0.92 (3H, d, J=6.2 Hz), 0.89 (3H, s), 0.84 (3 H, d, J=6.8 Hz), 0.70 (3H, s), 0.61 (3H, d, J=6.7 Hz) and 0.56 (3H, s) ppm;

MS m/z (%) 507 (M$^+$–1, 1), 465 (2), 327 (3), 199 (100), 183 (13), 135 (26), 111 (38), 69 (80) and 57 (35).

EXAMPLE 17

Preparation of (1R,3R)-(3-((1S,4R)-4-(tert-butyl-diphenylsilyloxy-methyl)-1,5-dimethylhexyl)-2,2,3-trimethyl)cyclolpentanecarbaldehyde (19)

Intermediate (18) (0.023 g, 0.047 mmol) was oxidized by a Swern oxidation method according to the procedure described above for intermediate 10. The crude residue obtained was purified by HPLC over silica (isooctane/ethyl acetate, 98:2) to afford 0.021 g (92% yield) of the desired intermediate (19) which was characterized as follows:

$R_f$ (isooctane/EtOAc, 98:2) 0.14;

IR (KBr film) absorption bands at 2962, 1717, 1472, 1428, 1384, 11111, 1050, 822 and 703 cm$^{-1}$;

$^1$H NMR (500 MHz, CDCl$_3$) chemical shifts at 9.69 (1H, d, J=2.5 Hz), 7.68 (4H, m), 7.37 (6H, m), 3.52 (1H, m), 2.60 (1H, m), 1.93 (1H, m), 1.04 (9H, s), 0.90 (3H, d, J=6.7 Hz), 0.89 (3H, s), 0.86 (3H, d, J=6.8 Hz), 0.71 (3H, s) and 0.62 (3H, d, J=6.7 Hz) ppm; and MS m/z (%) 464 (M$^+$–42, 2), 449 (3), 311 (4), 233 (6), 199 (91), 183 (15), 135 (33), 109 (50), 69 (100) and 43 (65).

EXAMPLE 18

Preparation of 5-{(E)-3-[3-(4-tert-butyldiphenylsilyloxy-1,5-dimethyl-hexyl)-2,2,3-trimethyl-cyclopentyl]-allylidene}-1,3-bis(tert-butyl-dimethylsilyloxy)-cyclohexane (21)

To a solution of (3R,5R)-{bis(tert-butyldimethylsilyloxy)-cyclohexy-lidene]ethyl-diphenylphosphine oxide (20) (0.68 mmol) in dry THF (7.5 mL) was added dropwise n-BuLi (2.5 M solution in hexane; 0.24 mL, 0.60 mmol) at −78° C. under argon atmosphere. The formed dark red solution was stirred at −78° C. for 1 hour and a solution of intermediate (19) (0.17 mmol) in dry THF (2.5 mL) was added dropwise. The red solution was stirred at −78° C. for 2 hours and then allowed to slowly warm to room temperature. The reaction mixture was loaded onto a silica gel column and the reaction product eluted (n-hexane/ethyl acetate). The residue obtained was further purified by HPLC over silica to give afford the desired protected intermediate (21).

EXAMPLE 19

Preparation of (1R,3R)-5-{(E)-3-[(S)-3-((S)-4-hydroxy-1-(S)-methyl-5-methyl-hexyl)-2,2,3-trimethyl-cyclopentyl]-allylidene}-cyclohexane-1,3-diol (22)

To a solution of intermediate (21) (0.14 mmol) in THF (4 mL) was added n-Bu$_4$NF (1 M solution in THF; 2.1 mL, 2.1 mmol). The reaction mixture was stirred at room temperature for 12 hours and then loaded onto a silica gel column. The reaction product was eluted (n-pentane/Me$_2$CO) and further purified by HPLC over silica to afford 0.0035 g, (44% yield) of the desired product (22) which was characterized as follows:

R$_f$ (n-hexane/Me$_2$CO, 65:35) 0.24;

IR (KBr film) absorption bands at 3365, 2962, 1463, 1381, 1050, 971, 909, 811 and 734 cm$^{-}$; and $^1$H NMR (500 MHz, CDCl$_3$) chemical shifts at 6.20 (1H, dd, J=14.8, 10.9 Hz), 6.03 (1H, d, J=10.9 Hz), 5.58 (1H, dd, J=14.8, 8.7 Hz), 2.61 (1H, dd, J=13.4, 3.7 Hz), 2.47 (1H, m), 2.33 (1H, dd, J=13.4, 7.3 Hz), 2.16 (2H, m), 0.94 (3H, s), 0.92 (3H, d, J=6.9 Hz), 0.90 (3H, d, J=6.8 Hz), 0.83 (3H, d, J=6.7 Hz), 0.82 (3H, s) and 0.74 (3H, s) ppm.

EXAMPLE 20

Preparation of (1R,3S)-5-((Z,2E)-3-((1S,3R)-3-((1S,4R)-4-hydroxy-1,5-dimethylhexyl)-2,2,3-trimethyl-cyclopentyl)-2-propenylidene)-4-methylenecyclohexane-1,3-diol The synthesis follows scheme IV:

Scheme IV

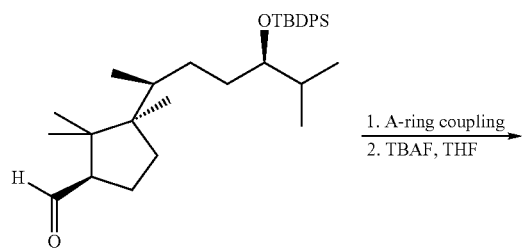

1. A-ring coupling
2. TBAF, THF

19

-continued

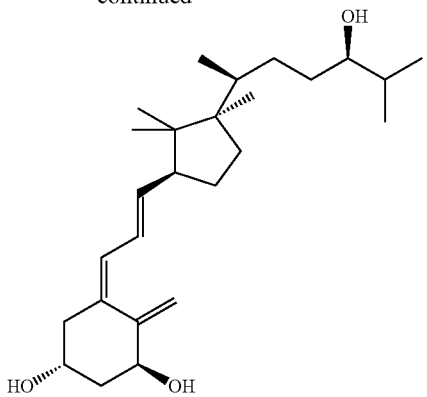

The aldehyde 19 prepared in example 17 (0.010 g, 0.020 mmol) was coupled with the appropriate A-ring phosphine oxide, and then deprotected using n-Bu$_4$NF according to the general procedure already described in example 19 above. The crude residue was purified by HPLC on silica gel (n-hexane/dimethylketone, 7:3 ratio) to provide the desired product (0.004 g, yield 48%), which was characterized as follows, together with the corresponding 24-OTBDPS derivative (0.0023 g, yield 18%).

Characterizing data for (1R,3S)-5-((Z,2E)-3-((1 S,3R)-3-((1S,4R)-4-hydroxy-1,5-dimethylhexyl)-2,2,3-trimethylcyclopentyl)-2-propenylidene)-4-methylene-cyclohexane-1,3-diol are as follows:

R$_f$ (n-hexane/Me$_2$CO, 65:35) 0.27;

IR (KBr film) bands at 3358, 2961, 1464, 1381, 1056, 983, 910 and 735 cm$^{-1}$;

$^1$H NMR (500 MHz, CDCl$_3$) shifts at 6.32 (1H, dd, J=15.1, 10.9 Hz), 6.08 (1H, d, J=10.9 Hz), 5.62 (1H, dd, J=15.1, 8.8 Hz), 5.32 (1H, d, J=1.0 Hz), 5.01 (1H, d, J=1.0 Hz), 4.45 (1H, br s), 4.20 (1H, br s), 3.31 (1H, br s), 2.58 (1H, dd, J=13.2, 3.8 Hz), 2.44 (1H, m), 2.28 (1H, m), 2.00 (2 H, m), 1.95 (1H, m), 0.93 (1H, d, J=6.7 Hz), 0.92 (3H, s), 0.90 (3H, d, J=6.8 Hz), 0.83 (3H, d, J=6.7 Hz), 0.81 (3H, s) and 0.74 (3H, s) ppm.

EXAMPLE 21

Synthesis of (3S,6S)-6-((1R,3R)-3-(tert-butyldiphenylsilyloxy-methyl)-1,2,2-trimethylcyclopentyl)-2-methylheptan-3-ol (53)

The synthesis follows scheme V below:

Scheme V

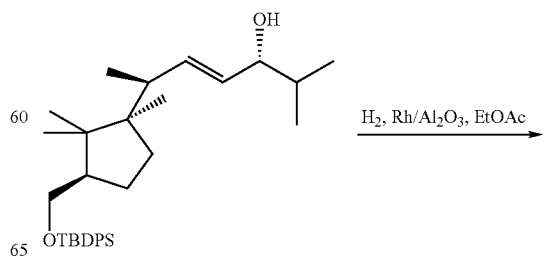

H$_2$, Rh/Al$_2$O$_3$, EtOAc

15

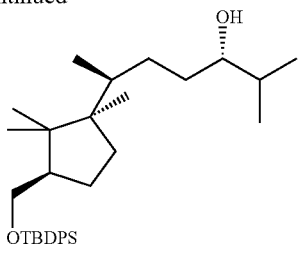

53

The intermediate isomer alcohol 15 prepared in example 13 (0.050 g, 0.10 mmol) was reduced as described above for the corresponding intermediate 14 in example 14. The crude product was purified by HPLC on silica gel (isooctane/ethyl acetate, 94:6) to give the saturated isomer alcohol 53 (0.045 g, yield 90%) which was characterized as follows:

$R_f$ (isooctane/EtOAc, 94:6) 0.26;

IR (KBr film) bands at 3370, 2960, 1472, 1428, 1380, 1112, 1070, 824, 738 and 702 cm$^{-1}$;

$^1$H NMR (500 MHz, CDCl$_3$) chemical shifts at 7.68 (4H, dd, J=7.7, 1.4 Hz), 7.39 (6H, m), 3.71 (1H, dd, J=10.0, 6.0 Hz), 3.52 (1H, dd, J=10.0, 7.7 Hz), 3.34 (1H, m), 2.11 (1H, m), 1.03 (9H, s), 1.02 (3H, d, J=6.8 Hz), 0.92 (3H, d, J=6.6 Hz), 0.81 (6H, s) and 0.74 (3H, s) ppm; and MS m/z (%) 508 (M$^+$, 1), 451 (1), 235 (14), 199 (100), 183 (14), 123 (52), 109 (84), 69 (75), 57 (56) and 43 (39).

EXAMPLE 22

Synthesis of (1R,3R)-(3-((1S,4S)-4-(tert-butyldiphenylsilyloxy-methyl)-1,5-dimethylhexyl)-2,2,3-trimethylcyclopentyl)methanol (54)

The synthesis follows scheme VI below:

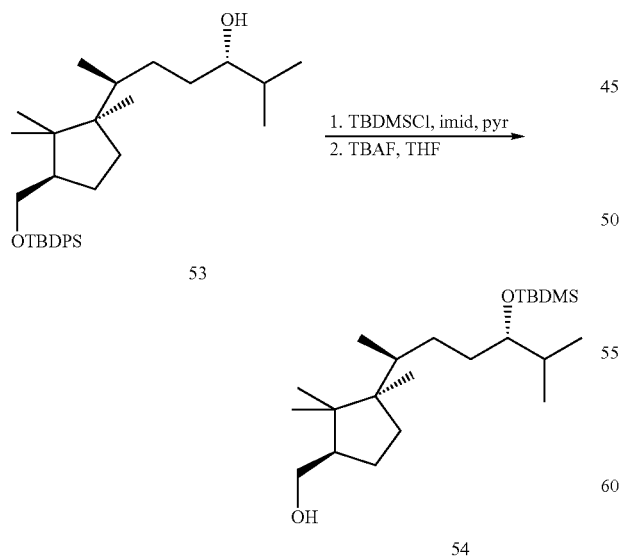

The isomer alcohol 53 prepared in example 21 (0.044 g, 0.089 mmol) was treated with TBDMSCl and TBAF as described above for the alcohol 16 in example 15. The crude product was purified by HPLC on silica gel (isooctane/ethyl acetate, 85:15 ratio) to give the primary alcohol 54 (0.0287 g, yield 65% over the two consecutive steps) which was characterized as follows:

$R_f$ (isooctane/ethyl acetate, 85:15) 0.23;

IR (KBr film) absorption bands at 3336, 2959, 1472, 1383, 1253, 1053, 837 and 772 cm$^{-1}$;

$^1$H NMR (500 MHz, CDCl$_3$) chemical shifts at 3.72 (1H, dd, J=10.1, 4.7 Hz), 3.48 (1H, dd, J=9.2, 9.2 Hz), 3.38 (1H, ddd, J=5.2, 5.1, 4.9 Hz), 2.08 (1H, m), 1.88 (1H, m), 1.69 (1H, m), 1.50 (2H, m), 1.29 (1H, m), 1.20 (1H, m), 1.08 (3H, s), 0.89 (9H, s), 0.85 (3H, d, J=7.0 Hz), 0.84 (3H, d, J=6.7 Hz), 0.82 (3H, s), 0.81 (3H, d, J=6.7 Hz), 0.75 (3H, s), 0.03 (3H, s) and 0.02 (3H, s) ppm; and MS m/z (%) 385 (M$^+$, 1), 341 (4), 327 (6), 313 (2), 235 (3), 213 (3), 187 (9), 123 (20), 83 (35) and 75 (100).

EXAMPLE 23

Synthesis of (1R,3R)-(3-((1S,4S)-4-(tert-butyldiphenylsilyloxy-methyl)-1,5-dimethylhexyl)-2,2,3-trimethyl)cyclopentanecarbaldehyde (55)

The synthesis follows scheme VII below:

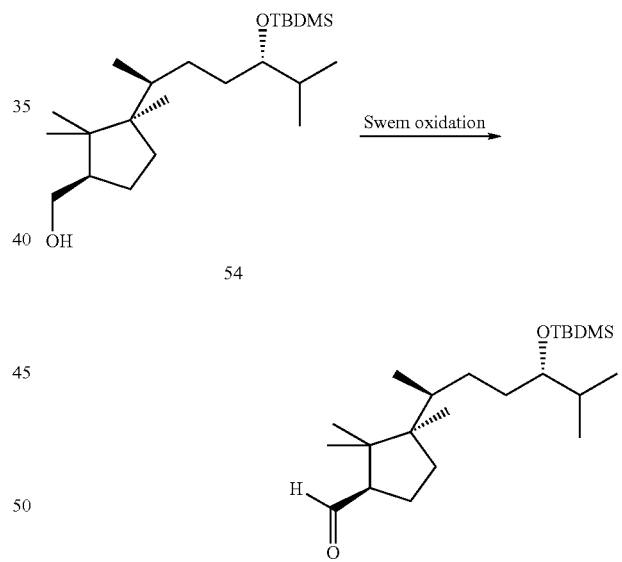

The alcohol 54 prepared in example 22 (0.028 g, 0.0728 mmol) was oxidized by Swern oxidation according to the hereinabove described procedure. The crude product was purified by HPLC on silica gel (isooctane/ethyl acetate, 99:1) to give the aldehyde 55 (0.0256 g, yield 92%) as a colourless oil which was characterized as follows:

$R_f$ (isooctane/ethyl acetate, 98:2) 0.25;

$[\alpha]_D^{18}$ −44.9 (c=0.592, CHCl$_3$);

IR (KBr film) bands at 2959, 1720, 1472, 1384, 1255, 1055, 837 and 773 cm$^{-1}$;

¹H NMR (500 MHz, CDCl₃) chemical shifts at 9.75 (1H, d, J=2.6 Hz), 3.39 (1H, m), 2.70 (1H, m), 2.00 (1H, m), 1.68 (3H, m), 1.52 (3H, m), 1.28 (3H, s), 1.20 (1H, m), 0.92 (3H, s), 0.89 (9H, s), 0.89-0.82 (15H, m) and 0.03 (6H, s) ppm.

EXAMPLE 24

Preparation of (1R,3S)-5-((Z,2E)-3-((1S,3R)-3-((1S,4S)-4-hydroxy-1,5-dimethylhexyl)-2,2,3-trimethyl-cyclopentyl)-2-propenylidene)-4-methylenecyclohexane-1,3-diol The synthesis follows scheme VIII:

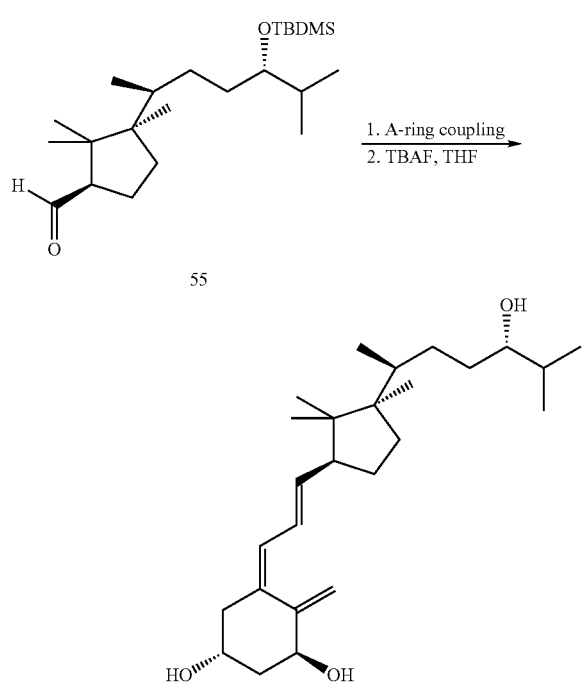

The aldehyde 55 prepared in example 23 (0.012 g, 0.031 mmol) was consecutively coupled with the appropriate A-ring phosphine oxide and then deprotected using TBAF (stirring for 3 days) according to the general procedure described above. The crude residue was purified by HPLC on silica gel (n-hexane/Me₂CO, 7:3) to give (1R,3S)-5-((Z,2E)-3-((1S,3R)-3-((1S,4S)-4-hydroxy-1,5-dimethylhexyl)-2,2,3-trimethylcyclopentyl)-2-propenylidene)-4-methylenecyclohexane-1,3-diol (0.012 g, yield 94%) which was characterized as follows:

R_f (n-hexane/dimethylketone, 65:35) 0.32;

$[\alpha]_D^{20}$+57.7 (c=0.880, CHCl₃);

IR (KBr film) bands at 3366, 2962, 1467, 1381, 1215, 1057, 982, 917 and 759 cm⁻¹;

¹H NMR (500 MHz, CDCl₃) chemical shifts at 6.32 (1H, dd, J=15.1, 10.9 Hz), 6.08 (1H, br d, J=10.9 Hz), 5.62 (1H, dd, J=15.1, 8.8 Hz), 5.32 (1 H, br s), 5.01 (1H, br s), 4.44 (1H, m), 4.21 (1H, m), 3.35 (1H, m), 2.58 (1H, dd, J=13.2, 3.9 Hz), 2.44 (1H, q, 9.3 Hz), 2.27 (1H, dd, J=13.2, 7.5 Hz), 1.97 (2H, m), 1.75-1.25 (15H, m), 0.93-0.88 (9H, m), 0.82 (3H, d, J=6.7 Hz), 0.82 (3H, s) and 0.75 (3H, s) ppm.

EXAMPLE 25

Binding Properties of 17-substituted D-ring Analogues Affinity for Vitamin D Receptor (VDR)

The methods used herein to evaluate the binding properties of vitamin D analogues are state of the art techniques used for steroid hormone (including vitamin D) binding assays. The affinity of 17-substituted D-ring analogues of 1,25(OH)₂D₃ to the vitamin D receptor was evaluated by their ability to compete with [³H]1α,25(OH)₂D₃ for binding to high speed supernatant from intestinal mucosa homogenates obtained from normal pigs. Incubation was performed at 4° C. for 20 hours and phase separation was obtained by addition of dextran-coated charcoal. The relative affinity of the analogues was calculated from the concentration needed to displace 50% of [³H]1α,25(OH)₂D₃ from its receptor compared with the activity of 1α,25(OH)₂D₃ (to which was assigned a value of 100%).

Affinity for Human Vitamin D Binding Protein (hDBP)

Binding of 1α,25(OH)₂D₃ analogues to hDBP was performed at 4° C. Briefly, [³H]1α,25(OH)₂D₃ and 1α,25(OH)₂D₃ or its analogues were added in 5 μl ethanol into glass tubes and incubated with hDBP (0.18 μM) in a final volume of 1 ml (0.01 M Tris-HCl buffer and 0.154 M NaCl, pH 7.4) for 3 hours at 4° C. Phase separation was then obtained by the addition of 0.5 ml of cold dextran-coated charcoal.

As shown in following table 1, all 17-substituted D-ring analogues of this invention displayed lower affinity for VDR compared with 1,25(OH)₂D₃. All analogues, except one with 40% affinity, showed no or very low (<10%) binding affinity for hDBP.

TABLE 1

| compound | side chain modification | VDR | DBP |
|---|---|---|---|
| 1,25(OH)₂D₃ | | 100 | 100 |
| (1R,3S)-5-((Z,2E)-3-((1S,3R)-3-((1S)-6,6,6-trifluoro-5-hydroxy-1-methyl-5-trifluoromethyl-3-hexynyl)-2,2,3-tri-methyl-cyclopentyl)-2-propenylidene)-4-methylenecyclohexane-1,3-diol | 20-epi-23-yne-26,27F6 | 75 | 2 |
| (1R,3S)-5-((Z,2E)-3-((1S,3R)-3-((1R)-6,6,6-trifluoro-5-hydroxy-1-methyl-5-trifluoromethyl-3-hexynyl)-2,2,3-tri-methylcyclopentyl)-2-propenylidene)-4-methylenecyclohexane-1,3-diol | 23-yne-26,27F6 | 60 | 0 |
| (1R,3S)-5-((Z,2E)-3-((1S,3R)-3-((1R)-5-hydroxy-1,5-dimethyl-3-hexynyl)-2,2,3-trimethylcyclopentyl)-2-propenylidene)-4-methylenecyclohexane-1,3-diol | 23-yne | 60 | 0 |
| example 24 | 24(R)OH | 20 | 4 |
| example 20 | 24(S)OH | 9 | 4 |
| (1R,3S)-5-((Z,2E)-3-((1S,3R)-3-((1S)-6,6,6-trifluoro-5-hydroxy-1-methyl-5-(trifluoromethyl)hexyl)-2,2,3-trimethyl-cyclopentyl)-2-propenylidene)-4-methylenecyclohexane-1,3-diol | 20-epi-26,27F₆ | 60 | 6 |
| (1R,3S)-5-((Z,2E)-3-((1S,3R)-3-((1R)-6,6,6-trifluoro-5-hydroxy-1-methyl-5-(trifluoromethyl)hexyl)-2,2,3-trimethyl-cyclopentyl)-2-propenylidene)-4-methylenecyclohexane-1,3-diol | 26,27F6 | 30 | 40 |
| MV2 | 23-yne-26,27F₆ | 50 | 7 |
| example 19 | 20-epi-24(R)OH | 3 | 4 |

TABLE 1-continued

| compound | side chain modification | VDR | DBP |
|---|---|---|---|
| (1R,3R)-5-((E)-3-((1S,3R)-3-((1S)-5-ethyl-5-hydroxy-1-methylheptyl)-2,2,3-trimethylcyclopentyl)-2-propenylidene)cyclohexane-1,3-diol | 20-epi-26,27-bishomo | 60 | <0.1 |

EXAMPLE 26

In Vivo Activity of 17-substituted D-ring Analogues

Eight weeks old, male NMRI mice were fed a vitamin D-replete diet (0.2% calcium, 1% phosphate, 2000 U vitamin D/kg; Hope Farms, Woerden, The Netherlands). Groups of six mice were intraperitoneally injected daily during 7 consecutive days with different doses of $1,25(OH)_2D_3$ (0.2 and 0.4 μg/kg/day) or analogues. The control group was injected with vehicle (arachis oil). The average weight of each group of 6 mice was determined at the beginning and at the end of the experiment. The following parameters were evaluated: serum calcium and femur calcium. Serum calcium was measured by a microcolorimetric assay (Sigma, St. Louis, Mo.). Femurs were removed and femur calcium content was measured in HCl-dissolved bone ash (obtained by heating for 24 hours in an oven at 100° C.), using the same technique as for serum calcium. Student's t-tests were carried out to detect significant differences; p<0.05 was accepted as significant.

Results

Several biological profiles were demonstrated in this first screening assay. As shown in table 2, the 21-hydrocarbon-17-substituted D-ring analogues of the present invention possess a desired and highly advantageous selectivity profile with no significant increase in serum calcium levels compared to vehicle treated animals together with significant increase in calcium content in bone. The preferential activity of the compounds on bone without major calcemic side effects allows the in vivo administration of this compound for the treatment of metabolic bone diseases where bone loss is a major concern.

TABLE 2

| Compound | Dose μg/kg/d | Serum calcium vs. control (%) | femur calcium vs. control (%) |
|---|---|---|---|
| Control | Arachis | 100 | 100 |
| 1,25(OH)₂Vit D3 | 0.2 | 121* | 97 |
| 1,25(OH)₂Vit D3 | 0.4 | 136* | 94* |
| (1R,3S)-5-((Z,2E)-3-((1S,3R)-3-((1S)-6,6,6-trifluoro-5-hydroxy-1-methyl-5-trifluoro-methyl-3-hexynyl)-2,2,3-tri-methyl-cyclopentyl)-2-propenylidene)-4-methylenecyclohexane-1,3-diol | 0.2 | 103 | 117* |
| (1R,3S)-5-((Z,2E)-3-((1S,3R)-3-((1R)-6,6,6-trifluoro-5-hydroxy-1-methyl-5-trifluoromethyl-3-hexynyl)-2,2,3-tri-methylcyclopentyl)-2-propenylidene)-4-methylenecyclohexane-1,3-diol | 0.4 | 94 | 115* |
| (1R,3S)-5-((Z,2E)-3-((1S,3R)-3-((1R)-5-hydroxy-1,5-dimethyl-3-hexynyl)-2,2,3-trimethylcyclopentyl)-2-propenylidene)-4-methylenecyclohexane-1,3-diol | 2 | 105 | 113* |
| example 24 | 0.2 | 98 | 112* |
| example 20 | 10 | 99 | 111* |

TABLE 2-continued

| Compound | Dose μg/kg/d | Serum calcium vs. control (%) | femur calcium vs. control (%) |
|---|---|---|---|
| (1R,3S)-5-((Z,2E)-3-((1S,3R)-3-((1S)-6,6,6-trifluoro-5-hydroxy-1-methyl-5-(trifluoro-methyl)hexyl)-2,2,3-trimethyl-cyclopentyl)-2-propenylidene)-4-methylenecyclohexane-1,3-diol | 0.05 | 106 | 112* |
| (1R,3S)-5-((Z,2E)-3-((1S,3R)-3-((1R)-6,6,6-trifluoro-5-hydroxy-1-methyl-5-(trifluoromethyl)hexyl)-2,2,3-trimethyl-cyclopentyl)-2-propenylidene)-4-methylenecyclohexane-1,3-diol | 0.4 | 98 | 114* |
| MV2 | 0.2 | 97 | 112* |
| example 19 | 5 | 100 | 115* |

*P < 0.05

EXAMPLE 27

Vitamin $D_3$ Analogue MV2 in an Ovariectomized Mice Model for the Primary Prevention of Osteoporosis Twelve-week-old C3H mice were randomly divided into four groups (9-13 mice/group). Two groups of mice were SHAM-operated (SHAM) and two groups were ovariectomized (OVX). Three days after the surgical procedure the SHAM and OVX mice were injected with MV2 intraperitoneally at 0.5 μg/kg/2days (4 times per week) or vehicle (arachis oil). The mice were treated for 8 weeks. At the beginning (before the first injection) of the experiment, bone mineral density (BMD) and bone mineral content (BMC) were determined by dual-energy X-ray absorptiometry (hereinafter referred as DEXA) and serum calcium levels were determined by a microcolorimetric assay. The animals were weighted regularly during the experimental period.

At the end of the experiment serum calcium levels, BMD and BMC were again measured. Trabecular and cortical bone mineral content (BMC) and bone mineral density (BMD) and the geometry of the femur were assessed by a Stratex XCT densitometer (pQCT). Femur calcium content was measured in HCl-dissolved bone ash (obtained by heating for 24 hours in an oven at 100° C.), using a microcolorimetric assay. Uterus was isolated from SHAM and OVX mice to check the estrogen depletion in ovariectomized mice demonstrated by uterus atrophy. Statistical analysis was performed with the software program NCSS (NCSS, Kaysville, Utah, USA). ANOVA analyses followed bye Fisher's least significant (LSD)-multiple comparison tests were carried out to detect significant differences, p<0.05 was accepted as significant.

Results are shown in the following tables 3 and 4 and in the appended figures.

Figure 1A:
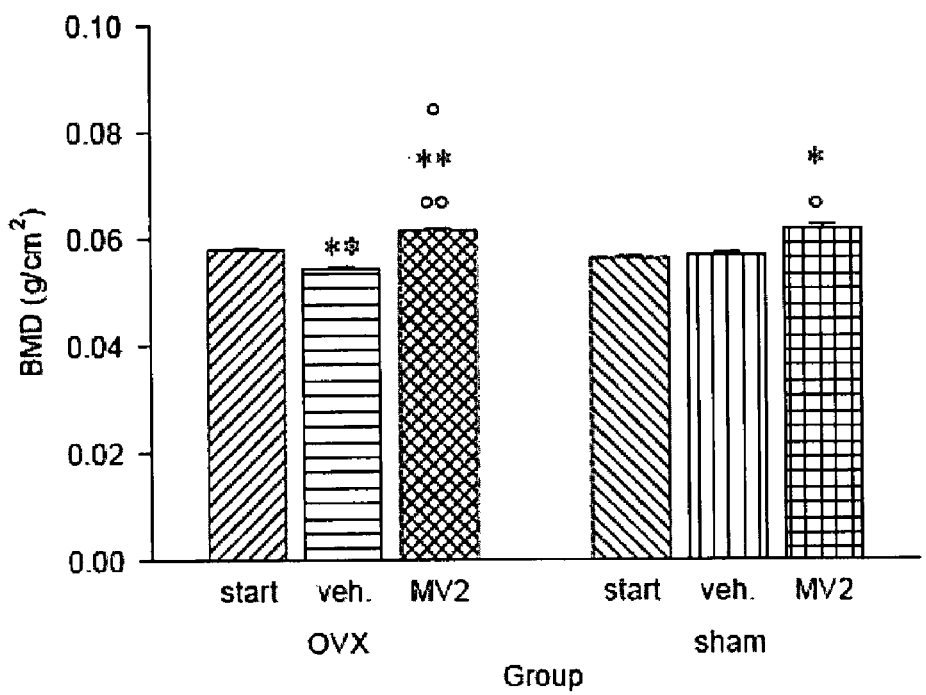
FIG. 1 shows data of the following experiment: 12-week old C3H mice were SHAM or OVX operated and treated with MV2, a vitamin $D_3$ analogue named (1R,3R)-5-((E)-3-((1S,3R)-3-((1R)-6,6,6-trifluoro-5-hydroxy-1-methyl-5-trifluoromethyl-3-hexynyl )-2,2,3-trimethylcyclopentyl )-2-propenylidene)cyclohexane-1,3-diol, (0.5 µg/kg/day intraperitoneously, i.p.) or vehicle (veh., arachis oil) during 8 weeks. The data for BMD of total body (FIG. 1A) and spine (FIG. 1B) and BMC of spine (FIG. 1C) are accompanied by the following notations.
Figure 1B:
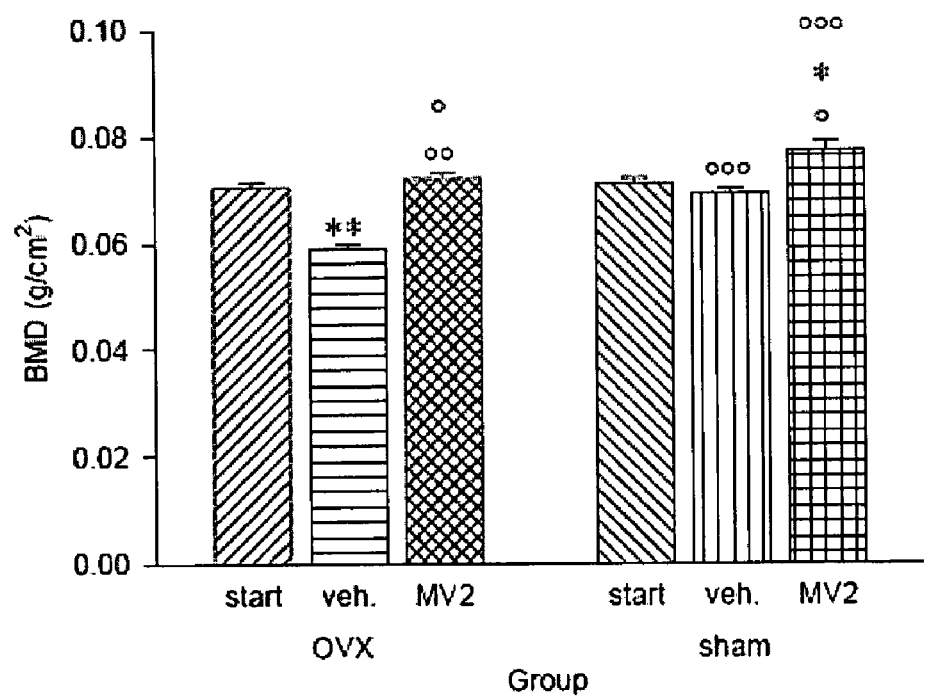
Figure 3A:
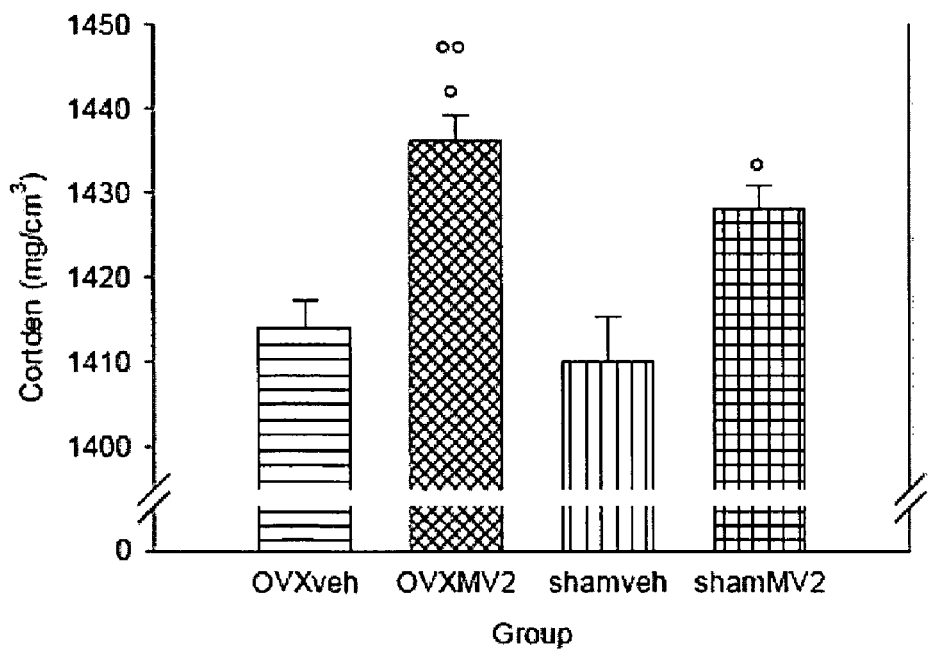
Figure 3B:
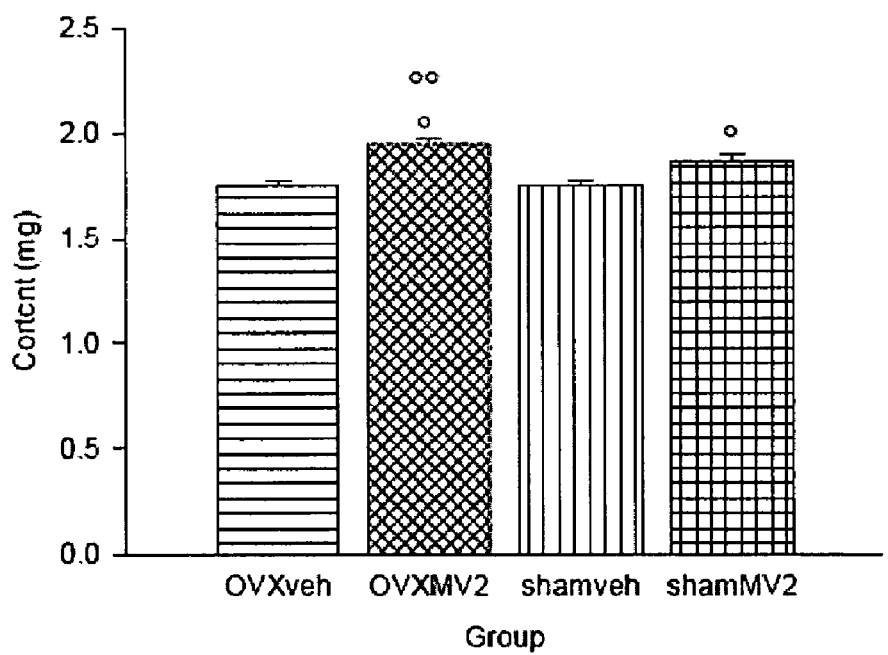
Figure 3C:
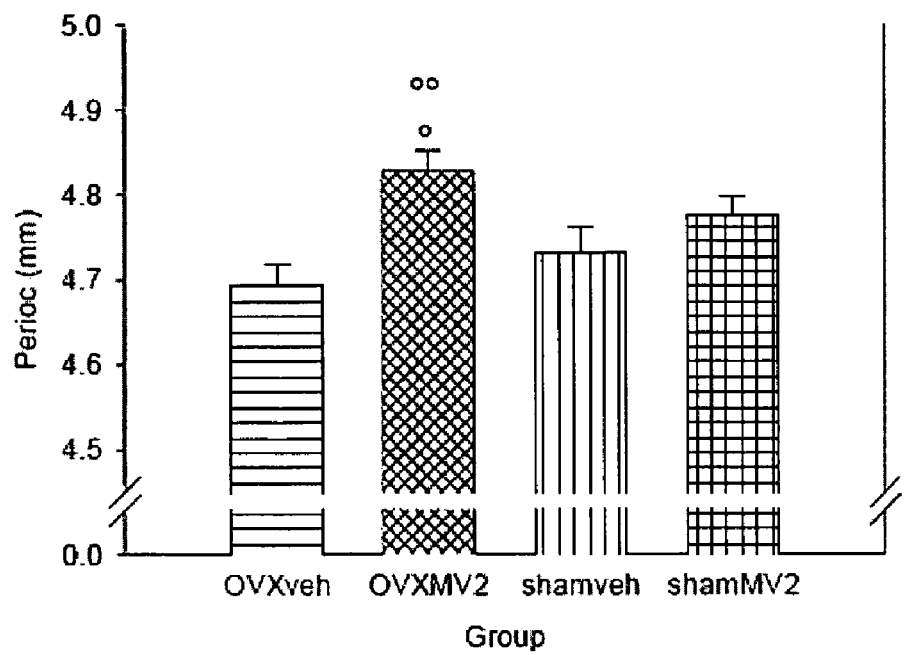
Figure 3D:
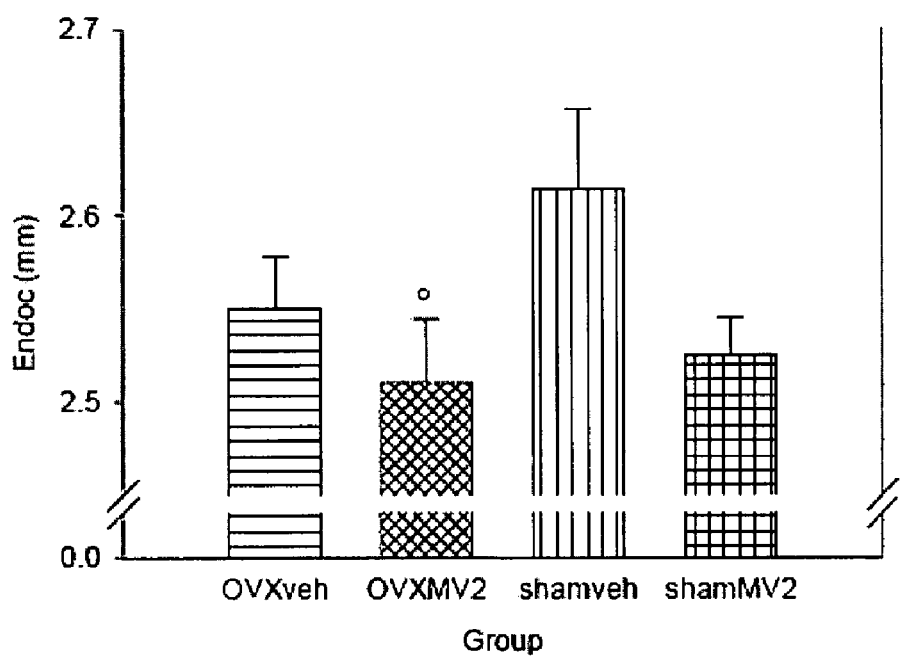
Figure 3E:
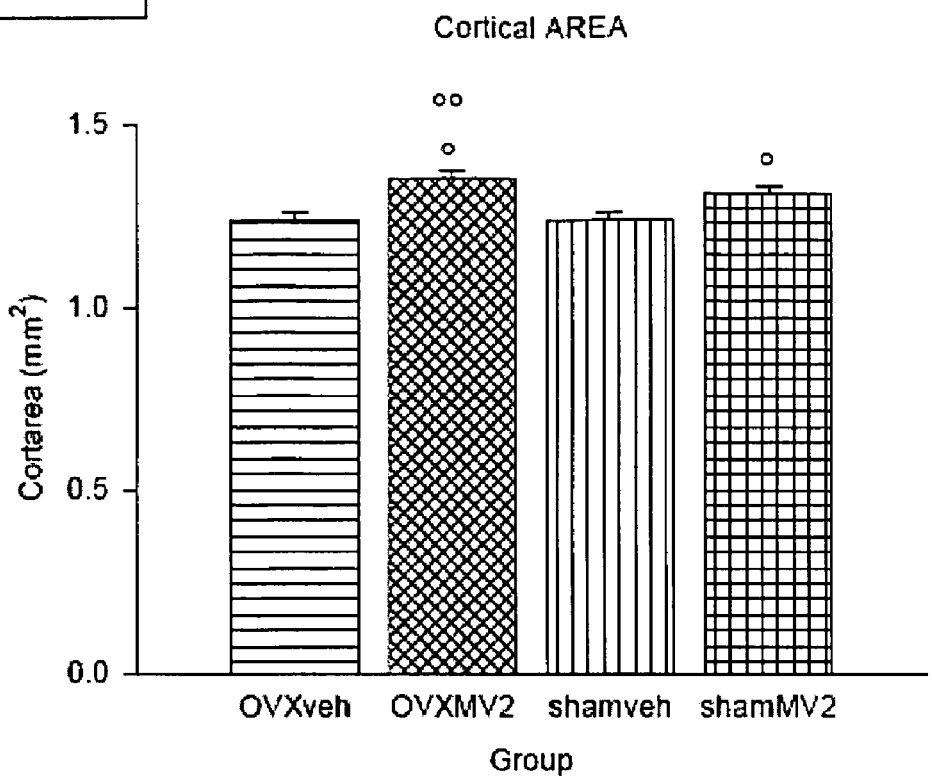
Figure 3F:
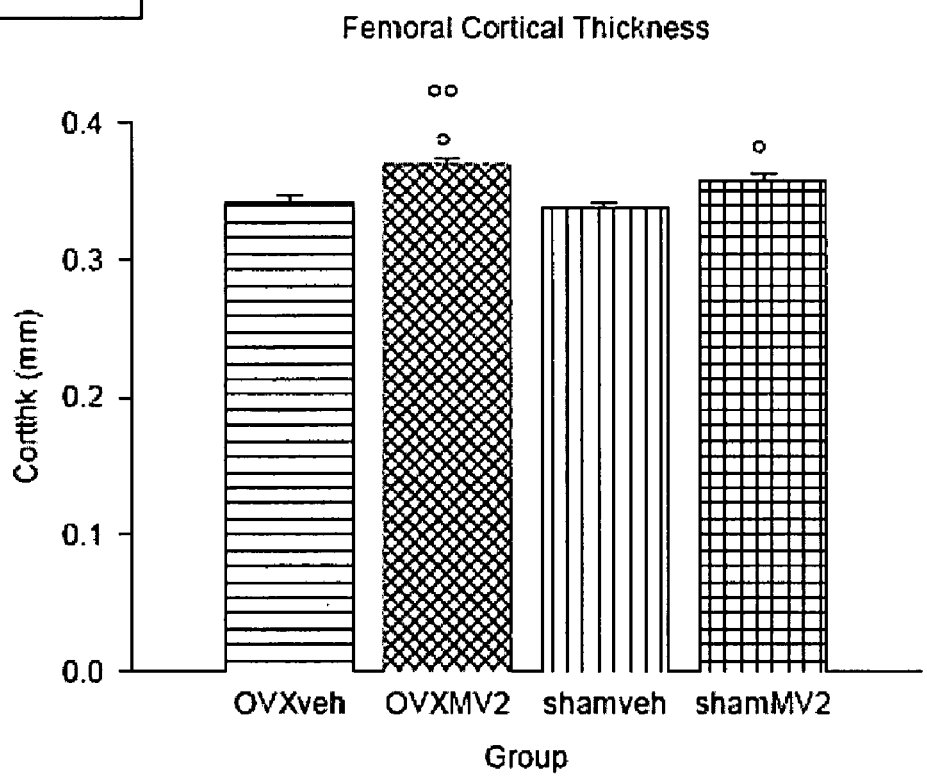

FIGS. 1A and B show that estrogen depletion in OVX animals significantly decreased BMD of total body (FIG. 1A, 6%) and of spine (FIG. 1B, 16%) at the end of the experiment. Eight-week treatment with MV2 prevented bone loss of OVX mice and increased BMD of total body (FIG. 1A, 9%) and of spine (FIG. 1B, 22%). Not only BMD but also BMC of total body was increased with 19 % compared to the OVX mice injected with vehicle (FIG. 1C). This vitamin D analogue is not only extremely effective in restoring bone mass of ovariectomized mice but it increases bone mass above SHAM-operated controls. MV2 increased BMD of total body (9%, FIG. 1A), BMD of spine (11%, FIG. 1B) and BMC (16%, FIG. 1C) in SHAM-WY1048 mice versus SHAM-vehicle mice. The results of DEXA were confirmed by pQCT of the femur in trabecular (FIGS. 2A-C) as well as in cortical bone (FIGS. 3A-B). The periosteal circumference was increased with 3% in OVX mice treated with the analogue compared to the OVX control mice (FIG. 3C). No significant effect was presented in the endosteal circumference (FIG. 3D). Due to the increase in periosteal circumference the cortical thickness and area of the femur was increased in OVX mice injected with the analogue compared to OVX control mice (FIGS. 3E-3F). The increased bone mass provided by MV2 translates into marked increase in bone strength demonstrated by significant increase in moment of inertia and resistance (FIGS. 4A-4B). The increased bone mineral content measured by DEXA and pQCT is also reflected by an increase in calcium content in femur in OVX treated animals (14%) as well as SHAM treated animals (12%) compared to their respective control animals (FIG. 5A). The potent effects of this compound on bone is again demonstrated by the fact that the calcium content in the femur of OVX treated animals is significantly higher than the SHAM-vehicle animals (FIG. 5A). Of great importance is that at the dose used in this study no hypercalcemic effects were seen (serum calcium levels below 11.5 mg/dl, FIG. 5B). Moreover no animals lost weight during the 8 weeks of treatment (FIG. 5C). All these data together show the existence of a safety window in which ANA-8 can be used to increase bone mineral content without elevating serum calcium levels.

TABLE 3A

| pQCT Femur | OVX analogue versus OVX vehicle (=100%) in % | SHAM analogue versus SHAM vehicle (=100%) in % |
|---|---|---|
| TRABECULAR BONE | | |
| Trabecular BMC | 69 ↑ | 83 ↑ |
| Trabecular BMD | 57 ↑ | 74 ↑ |
| Trabecular area | 8 ↑ | 7 ↑ |
| CORTICAL BONE | | |
| Cortical BMC | 11 ↑ | 7 ↑ |
| Cortical BMD | 2 ↑ | 1 ↑ |
| Cortical area | 9 ↑ | 6 ↑ |
| Cortical thickness | 8 ↑ | 6 ↑ |
| Periosteal circumference | 3 ↑ | 1 ↑* |
| Endosteal circumference | 2 ↓* | 4 ↓* |
| Moment of inertia | 12 ↑ | 6 ↑* |
| Moment of resistance | 8 ↑ | 3 ↑* |

*= not significant

TABLE 3B

| DEXA | OVX + analogue vs. OVX + vehicle (= 100%) in % | SHAM + analogue vs. SHAM + vehicle (= 100%) in % |
|---|---|---|
| BMD total body | 9 ↑ | 9 ↑ |
| BMC total body | 19 ↑ | 16 ↑ |
| BMD spine | 22 ↑ | 11 ↑ |

Besides injecting the compound MV2 intraperitoneally (results in table 3), it was also given orally by gavage in normal (no surgery) C3H female mice and the biological effects were investigated as described before. MV2 given orally at a dose of 1 µg/kg/2days (3 times per week) during 5 weeks was as effective as intraperitoneal injections at a dose of 0.5 µg/kg/2 days (4 times per week) during 5 weeks in C3H mice (Table 4). Again serum calcium levels were not enhanced (control mice 11.43±0.78 mg/dl versus analogue treated mice 11.36±0.56 mg/dl) demonstrating the therapeutic safety of this substance.

TABLE 4

| DEXA | SHAM + vitaminD analogue vs. SHAM + vehicle (= 100%), 0.5 µg/kg/2 days i.p. 4 times per week in % | SHAM + vitaminD analogue vs.SHAM + vehicle (= 100%) 1 µg/kg/2 days orally 3 times per week in % |
|---|---|---|
| BMD total body | 4 ↑ | 5 ↑ |
| BMC total body | 7 ↑ | 10 ↑ |
| BMD spine | 9 ↑ | 14 ↑ |

EXAMPLE 28

Restoration of Bone Loss by the 1α,25(OH)$_2$D$_3$ Analogue MV2

12-week-old C3H female mice were subjected to bilateral ovariectomy (OVX) or sham surgery SHAM (time point −3). The OVX and SHAM animals were treated with the vitamin D analogue MV2 (1 µg/kg three times per week) or vehicle (arachis oil) by oral gavage. Dosing was started 3 weeks after surgery (time point 0) and was continued for 8 weeks (time point 8). The number of mice per group is 8 to 10.

Before the surgery and 3 weeks after ovariectomy in vivo, measurements were performed in order to determine bone mineral density (BMD), bone mineral content (BMC) of total body and spine by DEXA. Before the surgery and 3 weeks after ovariectomy, serum was collected to measure calcium levels by a standard calorimetric method (Synchron CX4, Beckman Instruments, USA). The animals were weighted regularly during the experimental period to monitor their overall health and well being. After 4 weeks treatment, serum was again collected and biochemical parameters were determined. At the end of the experiment (8 weeks of treatment) bone mineral density (BMD) and bone mineral content (BMC) of total body and spine were measured by DEXA and serum was collected to determine serum calcium levels. After killing the animals, tibiae and femora were dissected. Tibiae were used for histomorphometric analysis, and femurs for measurement of cortical and trabecular volumetric density and geometry by peripheral quantitative computed tomography (PQCT) ex vivo. Statistical analysis was performed with the software program NCSS (NCSS, Kaysville, Utah, USA). ANOVA analyses followed bye Fisher's least significant (LSD)-multiple comparison tests were carried out to detect significant differences, p<0.05 was accepted as significant.

FIGS. 6 and 7 show that estrogen depletion in OVX animals significantly decreased BMD of total body (FIG. 6) and of spine (FIG. 7) three weeks after ovariectomy and this bone loss (OVX vehicle) is still present at the end of the experiment. Eight-week treatment with the vitamin D analogue MV2 prevented bone loss of OVX mice and increased BMD of total body (FIG. 6, 11%) and of spine (FIG. 7, 23%) when compared to the OVX mice treated with vehicle. Not only BMD but also BMC of total body (FIG. 8) and spine (FIG. 9) was increased with 12% and 25% respectively compared to the OVX mice treated with vehicle. This vitamin D$_3$ analogue is not only extremely effective in restoring bone mass of ovariectomized mice but it also increases their bone mass above the level of SHAM-operated controls (FIGS. 6 and 7). Beside the bone effects on OVX mice, MV2 increased BMD of total body (9%, FIG. 6) and spine (15%, FIG. 7); and increased BMC of total body (18%, FIG. 8) and spine (28%, FIG. 9) in SHAM-treated mice versus SHAM-vehicle mice. Of great importance is that at the dose (1 pg/kg three times per week) used in this study, no hypercalcemic effects were observed (FIG. 10). Moreover no animals lost weight during the 8 weeks of treatment (FIG. 11).

TABLE 5

| DEXA | OVX analogue versus OVX vehicle (= 100%) 1 µg/kg p.o. 3 times per week | SHAM analogue versus SHAM vehicle (= 100%) 1 µg/kg p.o. 3 times per week |
| --- | --- | --- |
| BMD total body | 11% ↑ | 9% ↑ |
| BMD spine | 23% ↑ | 15% ↑ |
| BMC total body | 12% ↑ | 18% ↑ |
| BMD spine | 25% ↑ | 28% ↑ |

All these data together show the existence of a broad safety dose window in which the vitamin $D_3$ analogue MV2 can be used to prevent or restore bone loss in mice without elevating serum calcium levels, thus demonstrating the therapeutic safety of this anti-osteoporotic agent.

COMPARATIVE EXAMPLE 29

Two vitamin D-ring analogues disclosed in U.S. Pat. No. 6,548,715 (example 37=17-methyl, 21-nor, natural side chain; and example 39=17-methyl, 21-nor, 20-ene, 23-ene respectively) were tested in the same biological procedures as in the previous examples. Table 6 below shows that they exhibit no selectivity for bone effects. These two compounds were found to have significant increased or decreased serum calcium levels together with no significant effects on femur calcium levels compared to the vehicle treated animals. No animals at all the doses tested demonstrated significant increase on femur calcium levels compared to the vehicle treated animals. The biological profile of these vitamin D analogues is therefore unfavorable for a therapeutic use in bone disorders.

TABLE 6

| | Dose µg/kg/day | Serum calcium versus control (%) | Femur calcium versus control (%) |
| --- | --- | --- | --- |
| Control | Arachis | 100 | 100 |
| 1,25(OH)₂Vit D3 | 0.2 | 121* | 97 |
| 1,25(OH)₂Vit D3 | 0.4 | 136* | 94* |
| example 37 | 0.4 | 95 | 104 |
| example 37 | 1 | 97 | 102 |
| example 37 | 5 | 95* | 99 |
| example 37 | 10 | 88* | 102 |
| example 37 | 20 | 98 | 100 |
| example 37 | 40 | 107* | 97 |
| example 37 | 100 | 104* | 98 |
| example 39 | 0.4 | 92 | 102 |
| example 39 | 5 | 97 | 101 |
| example 39 | 20 | 103 | 104 |
| example 39 | 40 | 109* | 102 |

*$p < 0.05$

Pharmaceutical Formulations

The present invention also relates to pharmaceutical compositions or formulations which comprise one or more of the novel vitamin $D_3$ compounds according to the present invention in admixture with one or more pharmaceutically acceptable excipients, diluents or carriers, the latter being for instance as described hereinafter.

For the purposes of the present invention the term "excipient" and "carrier" are used interchangeably throughout the description of the present invention and said terms are defined herein as, "ingredients which are used in the practice of formulating a safe and effective pharmaceutical composition." The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The vitamin $D_3$ analogues of this invention, when intended to be included in a pharmaceutical composition, may be formulated with conventional carriers and excipients, which can be selected in accordance with ordinary pharmaceutical practice. For instance, tablets may contain excipients, glidants, fillers, binders and the like. Aqueous formulations are preferably prepared in sterile form and, when intended for delivery by other than oral administration, are usually isotonic. Pharmaceutical formulations optionally contain excipients such as those set forth in the "Handbook of *Pharmaceutical Excipients*" (1986) and may include ascorbic acid and/or other antioxidants, chelating agents, carbohydrates such as dextrin-containing compounds (e.g. maltodextrins and/or cyclodextrins), hydroxyalkylcellulose, hydroxyalkylmethylcellulose, stearic acid and the like.

The term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the pharmaceutical compositions of this invention can suitably be in the form of concentrates, emulsions, solutions, granulates, dusts, sprays, aerosols, suspensions, ointments, creams, tablets, pellets or powders.

Suitable pharmaceutical carriers for use in the pharmaceutical compositions and formulations of the invention are well known to those skilled in the art. They also include additives such as, but not limited to, wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredient, in a one-step or multi-steps procedure, with the selected one or more carrier materials and, where appropriate, the other additives such as surface-active agents. They may also be prepared by micronisation, for instance in view to obtain them in the form of microspheres usually having a diameter of about 1 to 10 µm, namely for the manufacture of microcapsules for controlled or sustained release of the active ingredient.

Suitable surface-active agents, also known as emulsifiers, that can be used in the pharmaceutical compositions of the present invention include non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher ($C_{10}$-$C_{22}$) fatty acids, e.g. the sodium or potassium salts of oleic acid, stearic acid or natural fatty acid mixtures obtainable from coconut oil or tallow oil. Synthetic surfactants include sodium or calcium salts of polyacrylic acids; fatty sulphonates and sulphates; sulphonated benzimidazole derivatives preferably having 8 to 22 carbon atoms; and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Examples of alkylarylsulphonates are the sodium, calcium or alcanolamine salts of dodecylbenzene sulphonic acid or dibutyl-naphtalenesulphonic acid or a naphtalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose include natural (originating from animal or plant cells) or synthetic phospholipids of the cephalin or lecithin type such as, but not limited to, phosphatidylethanolamine, phosphatidylserine, phosphatidylglycerine, lysolecithin, cardiolipin, dioctanylphosphatidylcholine, dipalmitoylphoshatidylcholine and mixtures thereof in various proportions.

Suitable non-ionic surfactants include polyethoxylated and polypropoxy-lated derivatives of alkylphenols, fatty alcohols, fatty acids, aliphatic amines or amides containing at least 12 carbon atoms in the molecule, alkylarene-sulphonates and dialkylsulphosuccinates such as, but not limited to, polyglycol ether derivatives of aliphatic and cycloaliphatic alcohols, saturated and unsaturated fatty acids and alkylphenols, said derivatives preferably containing from 3 to 10 glycol ether groups and from 8 to 20 carbon atoms in the (aliphatic) hydrocarbon moiety and/or from 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing from 1 to 10 carbon atoms in the alkyl chain, which adducts contain from about 20 to 250 ethyleneglycol ether groups and/or from 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated $C_1$-$C_4$ alkyl, benzyl and/or hydroxy $C_1$-$C_4$ alkyl radicals.

A more detailed description of surface-active agents suitable for this purpose may be found for instance in "*McCutcheon's Detergents and Emulsifiers Annual*" (MC Publishing Group, Ridgewood, N.J., 1981), "Tensid-Taschenbuch", $2^{nd}$ ed. (Hanser Verlag, Vienna, 1981) and "Encyclopedia of Surfactants" (Chemical Publishing Co., New York, 1981).

The compound of this invention may be administered by any route appropriate for the bone disorder to be treated. Suitable routes include, but are not limited to, oral, rectal, nasal, topical (including transdermally, ocular, buccal and sublingual), vaginal and parenteral (including subcutaneous, intramuscular, intravenous, intra-arterially, intradermal, intrathecal and epidural) routes. The preferred route of administration may vary in accordance with certain clinical parameters, for example with the condition of the patient to be treated.

Pharmaceutical formulations of the present invention suitable for oral administration may be presented as discrete units such as capsules, cachets or tablets, each containing a predetermined amount of the active ingredient; as a powder or granules; as solution or a suspension in an aqueous liquid or a non-aqueous liquid; or as an oil-in-water liquid emulsion or a water-in-oil liquid emulsion. A suitable tablet may be made by compression or molding, optionally with one or more pharmaceutically acceptable inactive ingredients such as described hereinabove. Compressed tablets may be prepared by compressing, in a suitable compressing machine, the active ingredient in a free-flowing form such as a powder, granules, beads or pellets, optionally admixed with one or more pharmaceutically acceptable excipients such as binders, lubricants, inert diluents, preservatives, and surface-active or dispersing agents. Molded tablets may be made by molding, in a suitable molding machine, a mixture of the powdered active compound moistened with suitable amounts of one or more inert liquid diluents. The tablets may optionally be further coated, and may be formulated so as to provide slow or controlled release of the active ingredient therein.

The pharmaceutical formulations of the invention are optionally in the form of a topical ointment or cream. When formulated in an ointment, the active ingredient may be admixed with a paraffinic or water-miscible ointment base. Alternatively, the active ingredient may be formulated in a cream with an oil-in-water cream base. If desired, the aqueous phase of the cream base may include, for example, at least 30% by weight of a polyhydric alcohol, i.e. an alcohol having two or more hydroxyl groups either in a monomeric form such as, but not limited to, propylene glycol, butane-1,3-diol, mannitol, sorbitol and glycerol, or in a polymeric form such as polyethylene glycol (with various numbers of repeating units, including PEG 400) and mixtures thereof. Topical formulations may desirably include at least a compound which enhances absorption or penetration of the active ingredient through the skin or other areas of application. Examples of such dermal penetration enhancers include, but are not limited to, dimethylsulfoxide and related analogues. The solubility of the active compound of this invention in most pharmaceutically acceptable oils is quite high. Thus a cream formulation may suitably include one or more straight or branched chain, mono- or dibasic alkyl esters such as, but not limited to, di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP, the three latter being preferred esters. Alternatively, high melting point lipids such as white soft paraffin and/or liquid paraffin or other mineral oils can be used.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns, which may be administered by rapid inhalation through the nasal passage from a container. Suitable formulations wherein the carrier is a liquid, for administration as for example a nasal spray or as nasal drops, include oily solutions of the active ingredient.

When the pharmaceutical formulation is intended for a female patient, the active compound of the invention may be delivered into the systemic circulation through the vaginal mucosa from a vaginal device incorporated with a transmucosal vaginal composition. Said composition may be formulated and incorporated into the device as a suppository, cream, spray, gel, film, powder, foam, ointment, microcapsules, nanocapsules or a capsule containing microparticles or nanoparticles; and said vaginal device may be a vaginal tampon, vaginal ring, vaginal strip, vaginal capsule, vaginal tablet, vaginal pessary, vaginal cup or vaginal sponge; and said composition is delivered to the vaginal mucosa by inserting said device into the vagina.

Formulations suitable for parenteral administration include aqueous and non-aqueous sterile injection solutions which may contain anti-oxidants, buffers, bacteriostats and solutes which render the formulation isotonic with the blood of the patient; and aqueous and non-aqueous sterile suspensions which may include one or more suspending agents and/or thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or a weekly dose, as described herein, or an appropriate fraction thereof, of the active ingredient of this invention.

The present invention also provides controlled release pharmaceutical formulations, containing as an active ingredient the novel compound of the invention, in which the release of the active ingredient is controlled and regulated to allow less frequency dosing or to improve the pharmacokinetic or toxicity profile of said compound. Controlled release formulations adapted for oral administration in which discrete units comprising the compound of the invention can be prepared according to conventional methods in the art.

Additional ingredients may be included in order to control the duration of action of the active ingredient in the composition. Control release compositions may thus be achieved by selecting appropriate polymer carriers such as for example polyesters, polyamino-acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethylmethacrylate and other similar polymers. Such compositions include colloid drug delivery systems like liposomes, microspheres, microemulsions, nanoparticles, nanocapsules and the like. Depending upon the selected route of administration, the pharmaceutical composition may require protective coatings.

Non-limiting examples of compositions according to the present invention include:

a) from about 0.001 mg to about 1000 mg of (1R,3R)-5-{(E)-3-[(S)-3-((S)-4-hydroxy-1-(S)-methyl-5-methyl-hexyl )-2,2,3-trimethyl-cyclopentyl]-allylidene}-cyclohexane-1,3-diol; and b) one or more pharmaceutical excipients.

Another embodiment according to the present invention relates to the following compositions:

a) from about 0.01 mg to about 100 mg of (1R,3R)-5-{(E)-3-[(S)-3-((S)-4-hydroxy-1-(S)-methyl-5-methyl-hexyl)-2,2,3-trimethyl-cyclopentyl]-allylidene}-cyclohexane-1,3-diol; and b) one or more pharmaceutical excipients.

A further embodiment according to the present invention relates to the following compositions:

a) from about 0.1 mg to about 10 mg of (1R,3R)-5-{(E)-3-[(S)-3-((S)-4-hydroxy-1-(S)-methyl-5-methyl-hexyl)-2,2,3-trimethyl-cyclopentyl]-allylidene}-cyclohexane-1,3-diol; and b) one or more pharmaceutical excipients.

The terms "effective amount" and "therapeutic amount" as used herein may vary according to a range of factors known in the art, such as the disease state, age, sex, and weight of the human or animal being treated. Although particular dosage regimes are described herein, the person skilled in the art appreciates that these dosage regimes may be altered, after due consideration of said factors for each class of patients or each individual patient, in order to provide optimum therapeutic response. For example, several divided doses may be administered daily or the dose may be proportionally reduced as indicated by the requirements of the therapeutic situation. In addition, the compositions of the present invention can be administered as frequently as necessary to achieve a suitable therapeutic response in the patient being treated. For the purposes of the present invention a first aspect of "therapeutic amount" relates to compositions which deliver a compound according to the present invention wherein the plasma level of said compound is from about 0.1 pg/mL to about 100 mg/mL in humans or higher mammals. Another aspect relates to compositions which deliver a compound according to the present invention wherein said plasma level of said compound is from about 0.1 pg/mL to about 1 mg/mL in humans or higher mammals. Another aspect relates to compositions which deliver a compound according to the present invention wherein said plasma level of said compound is from about 1 pg/mL to about 1 mg/mL in humans or higher mammals. Yet another aspect relates to compositions which deliver a compound according to the present invention wherein said plasma level of said compound is from about 1 pg/mL to about 10 µg mg/mL in humans or higher mammals. Another aspect relates to compositions which deliver a compound according to the present invention wherein said plasma level of said compound is from about 1 ng/mL to about 25 mg/mL in humans or higher mammals.

Another aspect of the present invention relates to compositions which provide protection against bone loss, said compositions comprising:

a) a therapeutically effective amount of (1R,3R)-5-{(E)-3-[(S)-3-((S)-4-hydroxy-1-(S)-methyl-5-methyl-hexyl)-2,2,3-trimethyl-cyclopentyl]-allylidene}-cyclohexane-1,3-diol effective for preventing bone loss;

b) one or more pharmaceutically acceptable excipients.

In another embodiment the present invention includes compositions comprising:

a) a therapeutically effective amount of (1R,3R)-5-{(E)-3-[(S)-3-((S)-4-hydroxy-1-(S)-methyl-5-methyl-hexyl )-2,2,3-trimethyl-cyclopentyl]-allylidene}-cyclohexane-1,3-diol;

b) a therapeutically effective amount of one or more compounds having anti-inflammatory or pain relief properties; and c) one or more pharmaceutically acceptable excipients.

The following are non-limiting examples of compounds having pain relief properties or compounds which are effective in providing relief from pain and which can be suitably combined with the compounds of the present invention: acetaminophen, aspirin, difunisal, dipyrone, ibuprofen, naproxen, fenoprofen, fenbufen, ketoprofen, flurbiprofen, indomethacin, ketorolac, diclofenac, floctafenine, piroxicam, celecoxib, and rofecoxib.

The following are non-limiting examples of active ingredients which may be combined with the compounds of the present invention: caffeine, compatible amphetamines, compatible antihistamines, compatible anti-depressants; and opioid narcotic analgesics such as, but not limited to, oxycodone (Percadan, Percacet, Oxycontin, Tylox), pethidine/meperidine (Demerol), methadone (Physeptone, Dolophine), levorphanol (Dromoran, Levodromoran), hydromorphone (Dilaudid), and buprenorphine (Temgesic).

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

Method of Use

The present invention also relates to a method for controlling osteoporosis, bone loss and osteoarthritis in humans without the side effect of hypercalcemia. The present method comprises the step of administering to a human or higher mammal an effective amount of (1R,3R)-5-{(E)-3-[(S)-3-((S)-4-hydroxy-1-(S)-methyl-5-methyl-hexyl)-2,2,3-trimethyl-cyclopentyl]-allylidene}-cyclohexane-1,3-diol.

The compounds of the present invention can be used in the manufacture of one or more medicaments, non-limiting examples of which are:

i) a compound for use in the manufacture of a medicament for the treatment of osteoporosis;

ii) a compound for use in the manufacture of a medicament for the treatment of osteoarthritis;

iii) a compound for use in the manufacture of a medicament for the treatment of bone loss;

iv) a compound for use in the manufacture of a medicament for the treatment of osteoporosis without the side effect of inducing hypercalcemia;

v) a compound for use in the manufacture of a medicament for the treatment of bone loss without the side effect of inducing hypercalcemia.

While particular embodiments of the present invention have been illustrated and described, it is obvious to those skilled in the art that various other changes and modifications can be made without departing from the spirit and scope of the invention. It is therefore intended to cover in the appended claims all such changes and modifications that are within the scope of this invention.

The invention claimed is:

1. A vitamin $D_3$ analogue, (1R,3R)-5-{(E)-3-((1S,3R)-3-((1S,4R)-4-hydroxy-1,5-dimethylhexyl)-2,2,3-trimethylcyclopentyl)-2-propenylidene)cyclohexane-1,3-diol, represented by the structural formula:

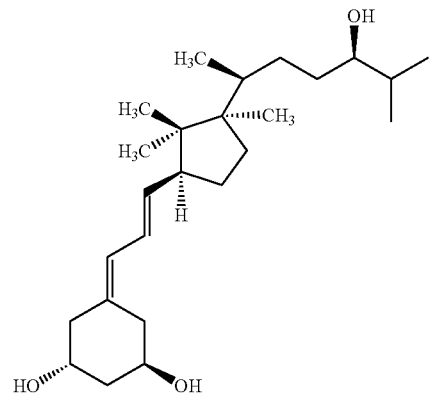

or a diastereomer thereof.

2. A vitamin $D_3$ analogue, (1R,3S)-5-((Z,2E)-3-((1S,3R)-3-((1S,4S)-4-hydroxy-1,5-dimethylhexyl)-2,2,3-trimethyl-cyclopentyl)-2-propenylidene)-4-methylene-cyclohexane-1,3-diol, having the structural formula:

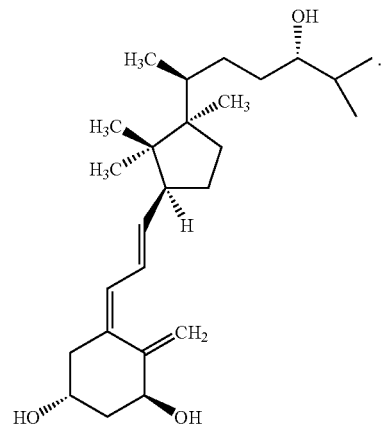

3. A vitamin $D_3$ analogue, (1R,3S)-5-((Z,2E)-3-((1S,3R)-3-((1S,4R)-4-hydroxy-1,5-dimethylhexyl)-2,2,3-trimethyl-cyclopentyl)-2-propenylidene)-4-methylene-cyclohexane-1,3-diol, having the structural formula:

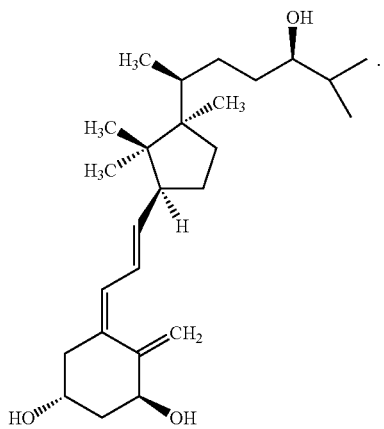

4. A pharmaceutical composition comprising a therapeutically effective amount of a vitamin D3 analogue selected from the group consisting of:

(1R,3R)-5-{(E)-3-((1S,3R)-3-((1S,4R)-4-hydroxy-1,5-dimethylhexyl)-2,2,3-trimethylcyclopentyl)-2-propenylidene)cyclohexane-1,3-diol, (1R,3S)-5-((Z,2E)-3-((1S,3R)-3-((1S,4S)-4-hydroxy-1,5-dimethylhexyl)-2,2,3-trimethylcyclopentyl)-2-propenylidene)-4-methylene-cyclohexane-1,3-diol, and (1R,3S)-5-((Z,2E)-3-((1S,3R)-3-((1S,4R)-4-hydroxy-1,5-dimethylhexyl)-2,2,3-trimethylcyclopentyl)-2-propenylidene)-4-methylene-cyclohexane-1,3-diol, and one or more pharmaceutically acceptable excipients, diluents or carriers.

5. A pharmaceutical composition according to claim 4, in the form of a dose comprising from 200 μg to 1 mg of said compound.

6. A composition for increasing bone mass in humans comprising an effective amount of a compound having the structural formula:

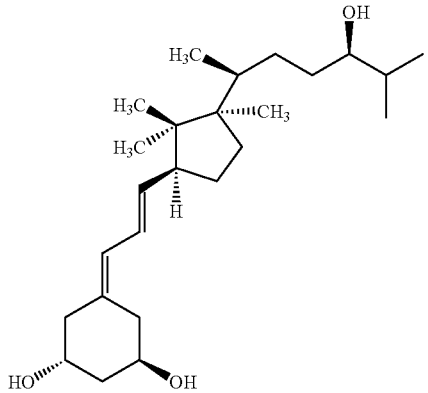

or a diastereomer thereof.

7. A composition for treating osteoporosis in humans comprising an effective amount of a compound having the structural formula:

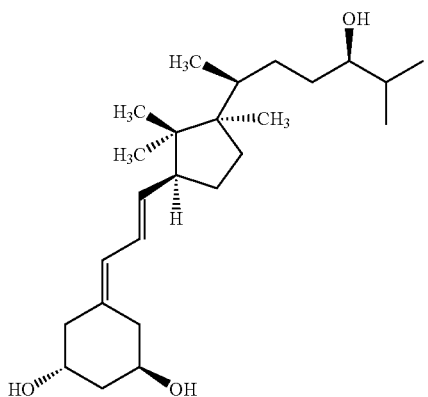

or a diastereomer thereof.

* * * * *